United States Patent
Montange et al.

(10) Patent No.: US 11,709,116 B2
(45) Date of Patent: Jul. 25, 2023

(54) LIQUID FLOURESCENT DYE CONCENTRATE FOR FLOW CYTOMETRY EVALUATION OF VIRUS-SIZE PARTICLES AND RELATED PRODUCTS AND METHODS

(71) Applicant: Sartorius BioAnalytical Instruments, Inc., Bohemia, NY (US)

(72) Inventors: Rebecca K. Montange, Louisville, CO (US); Jeffrey W. Steaffens, Broomfield, CO (US)

(73) Assignee: SARTORIUS BIOANALYTICAL INSTRUMENTS, INC., Bohemia, NY (US)

( * ) Notice: Subject to any disclaimer, the term of this patent is extended or adjusted under 35 U.S.C. 154(b) by 483 days.

(21) Appl. No.: 16/781,782

(22) Filed: Feb. 4, 2020

(65) Prior Publication Data
US 2021/0239581 A1 Aug. 5, 2021

(51) Int. Cl.
| | | |
|---|---|---|
| G01N 1/30 | (2006.01) | |
| C12Q 1/70 | (2006.01) | |
| G01N 15/14 | (2006.01) | |
| G01N 33/569 | (2006.01) | |
| G01N 33/58 | (2006.01) | |

(52) U.S. Cl.
CPC ........... G01N 1/30 (2013.01); C12Q 1/70 (2013.01); G01N 15/1404 (2013.01); G01N 33/56983 (2013.01); G01N 33/582 (2013.01); G01N 2001/302 (2013.01)

(58) Field of Classification Search
None
See application file for complete search history.

(56) References Cited

U.S. PATENT DOCUMENTS

| | | |
|---|---|---|
| 4,857,451 A | 8/1989 | Schwartz |
| 5,040,890 A | 8/1991 | North, Jr. |
| 5,245,318 A | 9/1993 | Tohge et al. |
| 5,306,467 A | 4/1994 | Douglas-Hamilton et al. |
| 5,321,130 A | 6/1994 | Yue et al. |
| 5,351,118 A | 9/1994 | Spinell |
| 5,374,398 A | 12/1994 | Isami et al. |
| 5,395,588 A | 3/1995 | North, Jr. et al. |
| 5,410,030 A | 4/1995 | Yue et al. |
| 5,483,469 A | 1/1996 | Van den Engh et al. |
| 5,602,039 A | 2/1997 | Van den Engh |
| 5,616,502 A | 4/1997 | Haugland et al. |
| 5,690,895 A | 11/1997 | Matsumoto et al. |
| 5,736,105 A | 4/1998 | Astle |
| 5,895,764 A | 4/1999 | Sklar et al. |
| 6,110,427 A | 8/2000 | Uffenheimer |
| 6,183,697 B1 | 2/2001 | Tanaka et al. |
| 6,248,590 B1 | 6/2001 | Malachowski |
| 6,256,096 B1 | 7/2001 | Johnson |
| 6,432,630 B1 | 8/2002 | Blankenstein |
| 6,550,324 B1 | 4/2003 | Mayer et al. |
| 6,589,792 B1 | 7/2003 | Malachowski |
| 6,592,822 B1 | 7/2003 | Chandler |
| 6,597,438 B1 | 7/2003 | Cabuz et al. |
| 6,664,047 B1 | 12/2003 | Haugland et al. |
| 6,813,944 B2 | 11/2004 | Mayer et al. |
| 6,878,556 B2 | 4/2005 | Sklar et al. |
| 6,880,414 B2 | 4/2005 | Norton |
| 6,890,487 B1 | 5/2005 | Sklar et al. |
| 7,016,022 B2 | 3/2006 | Fritz et al. |
| 7,061,595 B2 | 6/2006 | Cabuz et al. |
| 7,069,191 B1 | 6/2006 | Moore |
| 7,277,166 B2 | 10/2007 | Padmanabhan et al. |
| 7,307,721 B2 | 12/2007 | King |
| 7,318,336 B2 | 1/2008 | Roth et al. |
| 7,355,696 B2 | 4/2008 | Mueth et al. |
| 7,368,084 B2 | 5/2008 | Sklar et al. |
| 7,420,659 B1 | 9/2008 | Cabuz et al. |
| 7,452,725 B2 | 11/2008 | Leary et al. |
| 7,471,394 B2 | 12/2008 | Padmanabhan et al. |
| 7,485,153 B2 | 2/2009 | Padmanabhan et al. |
| 7,553,453 B2 | 6/2009 | Gu et al. |
| 7,671,987 B2 | 3/2010 | Padmanabhan et al. |
| 7,688,427 B2 | 3/2010 | Cox et al. |
| 7,691,636 B2 | 4/2010 | Frazier et al. |
| 7,754,421 B2 | 7/2010 | Transfiguracion et al. |
| 7,758,811 B2 | 7/2010 | Durack et al. |
| 7,776,268 B2 | 8/2010 | Rich |
| 7,780,916 B2 | 8/2010 | Bair et al. |

(Continued)

FOREIGN PATENT DOCUMENTS

| | | |
|---|---|---|
| CA | 2796489 A1 | 5/2014 |
| EP | 0822404 A2 | 2/1998 |

(Continued)

OTHER PUBLICATIONS

Suomalainen, Maarit et al., "Uncoating of non-enveloped viruses" SciVerse Science Direct, CurrentOpinion in Virology, www.sciencedirect.com, 2013, vol. 3, pp. 27-33.

Phelps, Donald K. et al., "Theoretical studies of viral capsid proteins", Current Opinion in Structural Biology, 2000, Department of Medicinal Chemistry, Purdue University, vol. 10, pp. 170-173.

Lin, Jun et al., "Structure of the Fab-Labeled 'Breathing' State of Native Poliovirus", Journal of Virology, downloaded from http://jvi.asm.og on Jan. 26, 2017; Mar. 7, 2012, vol. 86, No. 10, pp. 5959-5962.

Wang, Lintao et al., "Detecting structural changes in viral capsids by hydrogen exchange and mass spectometry", Protein Science, 2001, vol. 10, pp. 1234-1243.

(Continued)

Primary Examiner — Stacy B Chen
(74) Attorney, Agent, or Firm — Snell & Wilmer L.L.P.; Ross E. Breyfogle

(57) ABSTRACT

A kit and method for flow cytometry include a liquid dye concentrate for fluorescent staining of virus-size particles with a plurality of fluorogenic dyes in a liquid medium. The liquid dye concentrate includes a plurality of fluorogenic dyes and one or both of (i) the liquid medium comprising a liquid mixture including water and liquid phase organic material and (ii) disaccharide dissolved in the liquid medium.

35 Claims, 3 Drawing Sheets

(56) References Cited

U.S. PATENT DOCUMENTS

| | | |
|---|---|---|
| 7,817,276 B2 | 10/2010 | Kiesel et al. |
| 7,978,329 B2 | 7/2011 | Padmanabhan et al. |
| 7,981,661 B2 | 7/2011 | Rich |
| 8,017,402 B2 | 9/2011 | Rich |
| 8,071,051 B2 | 12/2011 | Padmanabhan et al. |
| 8,134,705 B2 | 3/2012 | Kaduchak et al. |
| 8,182,767 B2 | 5/2012 | Padmanabhan et al. |
| 8,187,888 B2 | 5/2012 | Rich |
| 8,202,733 B1 | 6/2012 | Javadi |
| 8,262,990 B2 | 9/2012 | Bair et al. |
| 8,263,955 B2 | 9/2012 | Kiesel et al. |
| 8,273,294 B2 | 9/2012 | Padmanabhan et al. |
| 8,283,177 B2 | 10/2012 | Ball et al. |
| 8,482,731 B2 | 7/2013 | Muraki |
| 9,546,936 B2 | 1/2017 | Rowlen et al. |
| 9,816,912 B2 | 11/2017 | Artinger et al. |
| 9,880,085 B2 | 1/2018 | Wilson et al. |
| 9,903,803 B2 | 2/2018 | Smolak et al. |
| 9,927,346 B2 | 3/2018 | Wilson et al. |
| 10,031,061 B2 | 7/2018 | Rowlen et al. |
| 10,041,103 B2 | 8/2018 | Bellinzoni et al. |
| 10,101,262 B2 | 10/2018 | Artinger et al. |
| 10,161,850 B2 | 12/2018 | Artinger et al. |
| 10,184,878 B2 | 1/2019 | Smolak et al. |
| 10,408,734 B2 | 9/2019 | Artinger et al. |
| 10,520,420 B2 | 12/2019 | Smolak et al. |
| 10,545,084 B2 | 1/2020 | Artinger et al. |
| 10,585,030 B2 | 3/2020 | Artinger et al. |
| 10,705,007 B2 | 7/2020 | Rowlen et al. |
| 10,739,246 B2 | 8/2020 | Artinger et al. |
| 11,137,337 B2 | 10/2021 | Gates et al. |
| 2003/0235919 A1 | 12/2003 | Chandler |
| 2005/0105077 A1 | 5/2005 | Padmanabhan et al. |
| 2006/0038989 A1 | 2/2006 | Domack et al. |
| 2006/0134002 A1 | 6/2006 | Lin |
| 2006/0163119 A1 | 7/2006 | Hirano et al. |
| 2006/0195268 A1 | 8/2006 | Vega |
| 2006/0259253 A1 | 11/2006 | Ellison et al. |
| 2008/0021674 A1 | 1/2008 | Puskas |
| 2008/0100840 A1 | 5/2008 | Oma et al. |
| 2008/0152542 A1 | 6/2008 | Ball et al. |
| 2008/0252884 A1 | 10/2008 | Carr |
| 2009/0023132 A1 | 1/2009 | Champseix |
| 2009/0029870 A1 | 1/2009 | Ward et al. |
| 2009/0104075 A1 | 4/2009 | Rich |
| 2009/0105963 A1 | 4/2009 | Laursen et al. |
| 2010/0261153 A1 | 10/2010 | Scholl et al. |
| 2010/0284016 A1 | 11/2010 | Teitell et al. |
| 2010/0319469 A1 | 12/2010 | Rich |
| 2011/0024615 A1 | 2/2011 | Tanner et al. |
| 2011/0089328 A1 | 4/2011 | Li |
| 2012/0077260 A1 | 3/2012 | Sharon et al. |
| 2012/0140205 A1 | 6/2012 | Kaduchak et al. |
| 2013/0050782 A1 | 2/2013 | Heng et al. |
| 2013/0080082 A1 | 3/2013 | Howes et al. |
| 2013/0137135 A1 | 5/2013 | Tai et al. |
| 2013/0171683 A1 | 7/2013 | Durack et al. |
| 2013/0252237 A1 | 9/2013 | Wagner |
| 2013/0327957 A1 | 12/2013 | Ayliffe |
| 2013/0338968 A1 | 12/2013 | Hanashi et al. |
| 2015/0132766 A1 | 5/2015 | Yasuda et al. |
| 2016/0273058 A1 | 9/2016 | Akashika et al. |
| 2017/0023570 A1 | 1/2017 | Reyes |

FOREIGN PATENT DOCUMENTS

| | | |
|---|---|---|
| EP | 1176412 A2 | 1/2002 |
| EP | 2652511 B1 | 5/2017 |
| KR | 20130128348 A | 11/2013 |
| WO | 9306482 A1 | 4/1993 |
| WO | 9636882 A1 | 11/1996 |
| WO | 2005059178 A1 | 6/2005 |
| WO | 2007103969 A2 | 9/2007 |
| WO | 2008010120 A2 | 1/2008 |
| WO | 2009093017 A1 | 7/2009 |
| WO | 2010132053 A1 | 11/2010 |
| WO | 2013147114 A1 | 10/2013 |
| WO | 2014062719 A2 | 4/2014 |
| WO | 2014210370 A1 | 12/2014 |
| WO | 2015187700 A2 | 12/2015 |
| WO | 2015187783 A1 | 12/2015 |
| WO | 2016048872 A1 | 3/2016 |
| WO | 2016154283 A1 | 9/2016 |
| WO | 2016154286 A1 | 9/2016 |
| WO | 2020028639 A1 | 2/2020 |
| WO | 2020197644 A1 | 10/2020 |

OTHER PUBLICATIONS

Bremner, K. Helen et al., Adenovirus Transport via Direct Interaction of Cytoplasmic Dynein with the Viral Capsid Hexon Subunit, Cell Host & Microbe Article, Dec. 17, 2009, vol. 6, pp. 523-535.

Varga, Mikael J. et al., "Antibodies with Specificities against a Dispase-Produced 15-Kilodalton Hexon Fragment Neutralize Adenovirus Type 2 Infectivity" Journal of Virology, vol. 64, No. 9, Sep. 1990, pp. 4217-4225.

Scherer, Julian et al., "Adenovirus Recruits Dynein by an Evolutionary Novel Mechanism Involving Direct Binding to pH-Primed Hexon", www.dmpi.com/journal/viruses, 2011, doi:10.3390/v3081417, vol. 3, pp. 1417-1431.

Salganik, Maxim et al., "Evidence for pH-Dependent Protease Activity in the Adeno-Associated Virus Capsid", Journal of Virology, downloaded from http://jvi.asm.org on Jul. 3, 2018; Nov. 2012, vol. 86, No. 21, pp. 11877-11885.

Moraes, Adolfo H. et al., "Antibody Binding Modulates Conformational Exchange in Domain III of Dengue Virus E Protein", Journal of Virology, downloaded from http://jvi.asm.org on Aug. 24, 2018; Feb. 2016, vol. 90, No. 4, pp. 1802-1811.

Haslwanter, Denise et al., "A novel mechanism of antibody-mediated enhancement of flavivirus infection", Plos Pathogens, https://doi.org/10.1371/journal.ppat.1006643, Sep. 15, 2017, pp. 1-27.

Brown, M.R., et al. "Flow cymetric quantification of viruses in activated sludge", Water Research, Elsevier, Amsterdam, NL, vol. 68, Oct. 8, 2014, pp. 414-422.

Safety Data Sheet Buffer Solution pH4, Carolina Biological Supply Company, Oct. 29, 2015, URL:https://www.lewisu.edu/academics/biology/pdf/pH%20Bufter"/"204.pdt [retrieved on May 15, 2020], 4 pages.

El-Hamalawi A-R A et al. "The Fluorometric Determination of Nucleic Acids in Pea Seeds by Use of Ethidium Bromide Complexes", Analytical Biochemistry, Academic Press, vol. 67, No. 2, Aug. 1, 1975, pp. 384-391.

"Virus Counter(R), Hardware Model: 3100, Software Version 3.0, Operation Manual", Sartorius; Rev B, Mar. 2018.

Rossi et al.; "Evaluation of ViroCyt Virus Counter for Rapid Filovirus Quantification"; Viruses; Feb. 20, 2015; 7; pp. 857-872.

Stoffel et al.; "Design and Characterization of a Compact Dual Channel Virus Counter"; Cytometry Part A, 65A, Wiley-Liss, Inc. (2005), pp. 140-147.

Wikipedia; "Virus Quantification"; http://en.wikipedia.org/wiki/Virus_quantification; 8 pgs, (2014).

Automation.com; "Honeywell Introduces High-Performance, Liquid Nano-Flow Sensor"; Jul. 30, 2004; 5 pgs.

Hercher et al.; "Detection and Discrimination of Individual Viruses by Flow Cytometry"; Journal of Histochemistry & Cytochemistry; Jan. 1, 1979; pp. 350-352.

Virus Counter(R), 3100 Reagent Kit, Part No. VIR-92333, Sartorius, 2018; Reference Doc: 3987, Effective Date Dec. 14, 2018, 1 page.

Matthiesen, Steen H et al., "Fast and Non-Toxic In Situ Hybridization without Blocking of Repetive Sequences", PLoS One, Jul. 2012, vol. 7, Issue 7, e40675, pp. 1-8.

Molecular Probes, "Electrophoretic Mobility-Shift Assay (EMSA) Kit (E33075)", Product Information MP33075, 2007, 4 pages.

Gates, Tyler et al., "Real Time Quantification of Lentivirus Particles Using Antibody-Based Detection on the Virus Counter® 3100 Platform", 2018, Sartorius Stedim Biotech, 4 pages.

(56) References Cited

OTHER PUBLICATIONS

Gates, Tyler et al., "Rapid, Real Time Quantification of Lentivirus Particles Using Antibody-Based Detection on the Virus Counter® 3100 Platform", Application Note, 2018, Sartorius, 4 pages.

Decherchi et al, "Dual staining assessment of Schwann cell viability within whole peripheral nerves using calcein-AM and ethidium homodimer", Journal of Neuroscience Methods., vol. 71, No. 2, 1997, pp. 205-213.

Natunen, Katariina et al., "Nile Red staining of phytoplankton neutral lipids: species-specific fluorescence kinetics in various solvents", J Appl Phycol, 2015, vol. 27, pp. 1161-1169 (published online Sep. 17, 2014).

Stacking (chemistry), Wikipedia, 10 pages, accessed Apr. 28, 2018.

S6653, SYPRO® Red protein gel stain, Safety Data Sheet, ThermoFisher Scientific, 2018, 9 pages.

Wong, Amy G. et al., "The dye SYPRO orange binds to amylin amyloid fibrils but not pre-fibrillar intermediates", Protein Science, 2016, vol. 25, pp. 1834-1840.

P3584, POPO™-3 iodide (534/570) *1 mM solution in DMF*, Safety Data Sheet, Life Technologies, 2013, 7 pages.

Zhegalova, Natalia G. et al, "Minimization of self-quenching fluorescence on dyes conjugated to biomolecules with multiple labeling sites via asymmetrically charged NIR fluorophores", Contrast Media Mol Imaging, 2014, vol. 9(5), pp. 355-362, NIH Public Access Author Manuscript.

SYPRO® Orange and SYPRO® Red Protein Gel Stains, Product Information, 2003, Molecular Probes, 5 pages.

Dimeric Cyanine Nucleic Acid Stains, Product Information, 2000, Molecular Probes, 4 pages.

Guryev, Oleg et al., "Control of the Fluorescence of Dye-Antibody Conjugates by (2-Hydroxypropyl)-β-cyclodextrin in Fluorescence Microscopy and Flow Cytometry", Analytical Chemistry, 2011, vol. 83, pp. 7109-7114.

Steinberg, Thomas H., Chapter 31, Protein Gel Staining Methods: An Introduction and Overview, Methods in Enzymology, vol. 463, 2009, pp. 541-563.

Hawe, Andrea et al., "Extrinsic Fluorescent Dyes as Tools for Protein Characterization", Pharmaceutical Research, vol. 25, No. 7, 2008, pp. 1487-1499.

Handbook of Flourescent Probes and Research Products, 2002, Molecular Probes, Table of Contents (2 pages), and pp. 1-6 (Introduction), 269-287 (Section 8.1, Nucleic Acid Stains), 355-377 (Section 9.1, Introduction to Protein Detection, and Section 9.2, Quantification and Selective Purification of Proteins in Gels, on Blots and in Capillary Electrophoresis) and 909-950 (Master Product List), accessed at www.mobitec.de/probes/docs.

LIQUID FLOURESCENT DYE CONCENTRATE FOR FLOW CYTOMETRY EVALUATION OF VIRUS-SIZE PARTICLES AND RELATED PRODUCTS AND METHODS

BACKGROUND

Flow cytometry is an analytical technique for measuring physical and/or chemical properties of particles as they flow in a fluid sample through an investigation cuvette, commonly referred to as a flow cell, of a flow cytometer. Although a sample fluid may be investigated by subjecting the sample fluid to a variety of stimuli, radiation, typically in the form of light, is one common stimulus technique. Flow cytometry is an important analytical technique that has gained wide acceptance for analyzing particles of biological material, and in particular for investigating properties of cells. More recently, flow cytometry has been adapted for use to detect unassociated (free in solution) virus particles, typically referred to as virions, and other extremely small particles of biological material of a similar size to viruses, referred to as virus-size particles. Such virus-size particles typically have a size of smaller than one micron, smaller 500 nanometers and in many cases smaller than 300 nanometers, smaller than 200 nanometers or even smaller than 100 nanometers. Some virus-size particles have a size on the order of tens of nanometers, although many have a size of at least 10 nanometers, often at least 20 nanometers or even at least 30 nanometers or larger. There are many types of viruses and other virus-size particles that have a particle size in a range of from 20 nanometers to 300 nanometers. A used herein, particle size is a reference generally to the maximum cross-dimension of the particle (e.g., diameter of a sphere, length of a rod). Systems and procedures for accurately analyzing such small particles by flow cytometry has been challenging, including with respect to repeatability of analytical results.

Traditional flow cytometry for detection of particles of a size on the order of cells, which are often several microns in size or larger, rely upon particle identification through light scatter detection. Additional information about specific biological attributes (e.g., cell type or infection of the cell by a particular virus) of a particle identified through light scatter detection may be provided through supplemental use of fluorescent antibody stains that bind to particular biological binding sites, or epitopes, for which the fluorescent emission signature may be detected separately from light scatter detection. However, particle identification through light scatter detection is generally not practical for virus-size particles, as the small size of the particles becomes closer in size to the wavelength of light used as an excitation source for the flow cytometry evaluation. As a consequence, techniques have been developed for detection and analysis of fluorescent emission response to both identify the presence of a particle and also for determining particular particle attributes. An example of a flow cytometer designed for detection and counting of virus-size particles through the use of fluorescent stains is the Virus Counter® 3100 flow cytometer (Sartorius Stedim Biotech).

A very useful class of fluorescent stains for flow cytometry evaluation of virus-size particles are the so-called fluorogenic dyes. When in a free, unbound state in solution, a fluorogenic dye exhibits only a very weak fluorescent response (quantum yield) to an excitation light source. However, when the molecule orientation of the fluorogenic dye becomes conformationally more rigid when bound to a particle, the fluorescent quantum yield increases significantly, often by an order of magnitude or more relative to the fluorescent response of the fluorogenic dye in the free, unbound state. This permits the strong fluorescent signals of the bound dye molecules to be identified over the relatively weak background fluorescence from the unbound dye molecules. The functioning of fluorogenic dyes is significantly different than the functioning of traditional fluorophore stains, often in the form of fluorescent antibody stains, commonly used in flow cytometry evaluation of cells. Such fluorophore stains exhibit a strong fluorescent response whether bound to a particle or in a free, unbound state in solution.

One limitation on the use of fluorogenic dyes for staining virus-size particles is that the dyes tend to be nonspecific, and do not bind to a particular biological binding site, or epitope, as is the case with fluorescent antibody stains. One important technique for use of fluorogenic dyes flow cytometry evaluation for virus-size particles involves simultaneous staining with one fluorescent dye that non-specifically stains protein content and a second fluorescent stain that nonspecifically stains nucleic acid content (e.g., DNA, RNA). By using stain formulations including a mixture of both types of fluorogenic dyes, detection of simultaneous occurrences of the fluorescent emission signatures of both of the nonspecific protein stain and the nonspecific nucleic acid stain is indicative of a particle that the particle may be an intact virus containing for example an envelope protein and genetic material, whereas detecting only one of the fluorescent signatures is indicative of a different type of particle not containing both the protein and nucleic acid attributes, for example a virus-like particle having protein content but not genetic material. This type of simultaneous use of multiple fluorogenic dyes for flow cytometry evaluation of virus-size particles has achieved significant success, for example in combination with use of the Virus Counter® 3100 flow cytometer. Still, formulating multiple fluorogenic dyes in a mixture having significant shelf life and that can be conveniently used to stain unassociated virus-size particles for flow cytometry evaluation with a high level of precision, or repeatability, has proved challenging. For example, a Combo Dye® reagent kit that has been available for use with the Virus Counter® flow cytometer includes a dry powder mixture of fluorogenic dyes for nonspecific protein staining and non-specific nucleic acid staining of unassociated virus-size particles and acetonitrile and aqueous buffer solution used to reconstitute the dry powder dye mixture into an aqueous liquid stain formulation that is added to a fluid sample containing biological material to simultaneously stain the fluid sample with both fluorogenic dyes. To prepare the aqueous liquid stain formulation, the dry powder mixture is mixed with the acetonitrile, or more recently dimethyl sultoxide (DMSO), to promote dissolution of the fluorogenic dyes into the acetonitrile and then after a 5-minute incubation period aqueous buffer solution is added to the mixture to prepare the aqueous liquid stain formulation that is then added to the fluid sample containing the biological material to be stained for flow cytometry evaluation for unassociated virus-size particles. One example of such a dry powder mixture includes a mixture of POPO™-3 iodide nucleic acid stain (ThermoFisher Scientific) and SYPRO™ Red protein stain (ThermoFisher Scientific). Such a kit has reasonable shelf life and is relatively easy to use to stain fluid samples for flow cytometry evaluation. However, even though such kits have had a level of success, there remains a need for stain products and staining techniques that provide improved flow cytometry performance when using multiple fluorogenic stains for flow cytometry evaluation for unassociated particles of virus size, including in terms of enhanced precision and repeatability of flow cytometry results.

SUMMARY

Self-quenching is a phenomenon in which fluorescence energy from fluorescent stains is consumed by energy transfer between dye molecules in close proximity to each other that effectively consumes the anticipated wavelength of light that otherwise might be emitted. Such close proximity of dye molecules that may cause quenching may result from overcrowding of dye molecules on a stained substrate, such as a particle. In the case of fluorogenic dyes, if dye molecules are susceptible to existing in aggregated forms in aqueous liquids, such as are typically used to prepare flow cytometry fluid samples and fluorogenic stains formulations for staining such fluid samples, such an aggregates of dye molecules attaching to a particle may have a significant propensity to self-quench a significant amount of fluorescent emission, and the presence of such aggregates on a stained particle, which may reduce the total strength of a fluorescent emission signal from a stained particle during flow cytometry. Such aggregates may also attain a size and form that will not attach to a particle, representing a loss of available stain, and such free aggregates may increase blank counts. Such impairment of fluorescent emission signals may have a pronounced negative effect on flow cytometry evaluation of stained particles of virus size, because of the smaller available area on such small particles to accommodate dye molecule attachment than on larger particles such as cells. Occupying portions of such available attachment area with dye molecule aggregates may significantly reduce the strength of the total fluorescent emission signal from a stained virus-size particle, and such self-quenching effects may impair precision of flow cytometry results, and repeatability of results between fluid samples. One measure of the precision of flow cytometry in flow cytometry results is the coefficient of variation (standard error or measurements divided by the mean of the measurements, often abbreviated as c.v.) which is an indication of the statistical variation of flow cytometry results between fluid samples of the same composition stained and processed in the same way. It has been found that different vials from a batch, or lot, of aqueous fluorogenic dye formulation prepared from dry powder fluorogenic dye mixtures reconstituted as summarized above using acetonitrile in the reconstitution process can vary significantly in flow cytometry performance, which is believed to be due to inconsistent solvation and dispersion of the fluorogenic dyes as present in the final aqueous stain formulation, leading to inconsistent staining and greater-than-desired variation in flow cytometry results. Sample-to-sample variations can be above 20% and day-to-day variations can be 30% or more. More particularly, it is believed that such inconsistent solvation and dispersion results in significant part from formation and/or persistence of dye molecules held in aggregates through pi stacking interactions in the aqueous liquid formulations of fluorogenic dye molecules used to stain fluid samples for flow cytometry evaluation. Pi stacking (which is also called π stacking or π-π stacking, or sometimes is simply referred to as "stacking"), refers to a noncovelant attraction that occurs between aromatic rings. Such interactions, for example, are involved with base stacking in three-dimensional structures of DNA and RNA molecules.

Another complication with the use of fluorogenic dyes is that some fluorogenic dyes have limited stability in aqueous stain formulations used to stain fluid samples, and stain formulation performance may deteriorate significantly over a short period of time following preparation, significantly limiting the useful shelf life for the stain formulation before use. A further complication with the use of fluorogenic dyes is that for some fluorogenic dyes, the dye molecules appear to aggregate in stain formulations and stained fluid samples in a manner such that when such aggregates are in a free state in solution, not attached to and staining a particle, the aggregates may sometimes become sufficiently fluorescent that during flow cytometry evaluation the fluorescent response from the free aggregates may be difficult to differentiate from stained particles of interest, which can lead to significant inaccuracies in particle counts determined by flow cytometry. One technique for correcting raw flow cytometry particle count results is to subtract from those raw results background particle counts determined from flow cytometry on blank fluid samples of the same or similar fluid matrix but without containing any particles. Such blank fluid samples are stained in the same manner as the fluid samples with biological material under investigation and are subjected to the same flow cytometry evaluation to determine a blank particle count that is then subtracted from raw particle counts from flow cytometry results on the fluid samples under investigation. However, fluorescent activity of some dye molecule aggregates may significantly increase background counts for some fluorogenic dyes, to a level where it may become difficult to meaningful distinguish between blank and real particle counts. The noted complications concerning stain formulation instability highly fluorescent dye molecule aggregates appear to be more associated with fluorogenic dyes that have higher hydrophobicity, such as is the case for example with SYPRO™ red protein stain.

More recently, it has been identified that use of dimethyl sulfoxide (DMSO) to reconstitute such a dry powder dye formulation into an aqueous formulation may significantly reduce problems associated with pi stacking in the reconstituted aqueous formulations, for example as disclosed in International Patent Application No. PCT/US2019/044623, the entire contents of which are incorporated herein by reference as is set forth herein in full. Dissolving a dry powder mixture with multiple different fluorogenic dyes a liquid medium with DMSO before dilution with added aqueous liquid to prepare final aqueous fluorogenic dye formulations that are used to stain fluid samples for flow cytometry evaluation for unassociated (free in solution) virus-size particles were identified as, surprisingly and unexpectedly, significantly reducing the coefficient of variation of flow cytometry results between fluid samples. It was also identified in International Patent Application No. PCT/US2019/044623 that performance of fluorogenic stain formulations prepared in aqueous liquid media may be significantly improved by including a significant quantity (although a minor quantity on a molar basis) of DMSO in the aqueous liquid medium of the fluorogenic stain formulation that is used to stain fluid samples, and which results in a significant quantity (although a minor quantity on a molar basis) of DMSO also being present in the final stained fluid sample that is then subjected to flow cytometry. Also, although the discussion in that reference was presented in relation to inclusion of such a significant quantity of DMSO in the aqueous fluorogenic stain composition, which was identified as preferred, the concept was identified as not so limited, identifying a similar beneficial effect may be obtained using other polar organic solvent liquids, for example acetonitrile.

It was also identified in International Patent Application No. PCT/US2019/044623 that problems associated with blank particle counts, thought to be attributable to aggregates of fluorogenic dye molecules, may be significantly reduced by including a disaccharide in the final stained fluid samples, both in stained blank fluid samples and in stained fluid samples with the biological material of interest for flow cytometry evaluation. It was thought that the presence of the disaccharide in solution in the stained fluid sample helps disperse and reduce aggregation of fluorogenic dyes, and particularly those that are more hydrophobic such as SYPRO™ red, to reduce possible detrimental effects of highly fluorescent dye molecule aggregates during flow cytometry. Surprisingly, including dissolved disaccharide in stained fluid samples was found to significantly reduce blank particle counts, where as including dissolved monosaccharide or trisaccharide was not found to provide any significant benefit and in some cases was detrimental.

However, even given these advances for use of multiple fluorogenic dye stain compositions, dry powder dye formulations continue to be difficult and complex to use, including processing required for reconstitution of the fluorogenic dyes in aqueous liquid media prior to staining a fluid sample for flow cytometry evaluation for unassociated virus-size particles. In addition to requiring significant personnel time to perform the reconstitution, the reconstitution processing adds complexity to the operation and opportunities for error and processing variation that can affect the repeatability of flow cytometry results. Inclusion of the fluorogenic dyes in a dry powder dye formulations for fluorescent staining products, such as in the Combo Dye® reagent kit, also increases complexity and cost to prepare the dry powder dye formulations. Even with these complexities, such dry powder dye compositions have continued to be used, because the fluorogenic dyes are stable and have good shelf life in the dry powder forms. However it has now been found that fluorogenic dye mixtures may be formulated in a liquid dye concentrate that exhibits a desirable combination of fluorogenic dye stability, shelf life and flow cytometry performance, at least comparable to the use of dry powder mixtures of fluorogenic dyes, while avoiding the problems presented by manufacture and use of such dry powder dye mixtures.

A first aspect of this disclosure is directed to a fluorescent stain product with multiple fluorogenic dyes for direct fluorescent staining of aqueous fluid samples containing biological materials with multiple fluorogenic dyes for flow cytometry evaluation of stained fluid samples for unassociated virus-size particles, the fluorescent stain product comprising:

a liquid dye concentrate comprising a plurality of different fluorogenic dyes in a liquid medium, each different said fluorogenic dye having a different fluorescent emission signature for detection when bound to a said unassociated virus-size particle; and a sealed container containing the liquid dye concentrate; and wherein the liquid dye concentrate comprises at least one member selected from the group consisting of:
(i) the liquid medium comprises a mixture including water and liquid phase organic material;
(ii) disaccharide dissolved in the liquid medium; and
(iii) a combination including both (i) and (ii).

A number of feature refinements and additional features are applicable to this first aspect of the disclosure. These feature refinements and additional features may be used individually or in any combination within the subject matter of this aspect or any other aspect of this disclosure. As such, each of the following features may, but are not required to be, used with any other feature or a combination of features of this aspect or any other aspect of this disclosure.

In preferred implementations, the liquid medium includes the liquid mixture with water and liquid phase organic material. The liquid phase organic material comprises at least one organic liquid component, and preferably comprises DMSO, and more preferably consists essentially of only DMSO. The liquid phase organic material may include one or more other liquid organic components other than or in addition to DMSO, for example acetonitrile. The liquid medium is preferably an aqueous liquid, that is with water making up the largest component of the liquid medium on a molar basis, and preferably the liquid medium is comprised of greater than 50 percent on a molar basis of water. More preferably, the liquid phase organic material only a small percentage on a molar basis of the liquid medium. As will be appreciated, the molecular weight of liquid organic components for the organic liquid phase material will tend to have higher molecular weights than water, and even if such liquid organic components make up a relatively large weight percentage of the liquid medium, the molar percentage for that liquid organic components may be substantially lower. For example, DMSO has a molecular weight of about 78 grams per mole, whereas water has a molecular weight of only about 18 grams per mole, meaning that a composition made up of 50 weight percent of each of DMSO and water comprises only about 19 percent by moles of DMSO. Similarly, acetonitrile has a molecular weight of about 41 grams per mole, also significantly larger than that of water, although not as large as DMSO.

In some preferred implementations, whether or not the liquid dye concentrate comprises disaccharide dissolved in a liquid medium, the liquid medium comprises the liquid phase organic material, such as DMSO, at a concentration of at least 10 weight percent, preferably at least 15 weight percent, and more preferably at least 20 weight percent. As the concentration of the liquid phase organic material is decreased to a very low level, the stability of the fluorogenic dyes in the liquid medium tends to decrease and flow cytometry performance may deteriorate. Conversely, problems may also arise as the concentration of the liquid phase organic material, such as DMSO, increases. One issue with a number of liquid organic components for the liquid phase organic material is that they tend to be very good solvents for a number of other materials. As a concentration of liquid phase organic material, such as DMSO, becomes larger, there is increased potential that the liquid phase organic material in the stained fluid sample may contribute to extraction of components from polymeric materials of fluidic components (e.g., polymeric materials of construction of tubing and valve parts) in flow cytometers or may be absorbed into and swell such fluidic components, either of which may be detrimental to flow cytometry performance. By maintaining the concentration of the liquid phase organic material relatively low in the liquid dye concentrate, the concentration of such liquid phase organic material is also maintained at a relatively lower concentration in the stained fluid sample than if the liquid dye concentrate contained a higher concentration of the liquid phase organic material. In some preferred implementations, whether or not the liquid dye concentrate includes disaccharide dissolved in liquid medium, the liquid medium comprises the liquid phase organic material, such as DMSO, at a concentration of no greater than 50 weight percent, preferably no greater than 35 weight percent and more preferably no greater than 30 weight percent. In some preferred implementations, whether or not the liquid dye concentrate comprises dissolved disaccharide, the liquid medium comprises at least 50 weight percent water, preferably at least 60 weight percent water, more preferably at least 65 weight percent water and even more preferably at least 70 weight percent water, however when the liquid medium comprises the liquid phase organic material, the liquid medium may typically comprise no greater than 90 weight percent water.

In some preferred implementations, the liquid dye concentrate comprises disaccharide dissolved in the liquid medium, and in even more preferred implementations the liquid dye concentrate comprises both disaccharide dissolved in liquid medium and that the liquid medium comprises a liquid mixture including water and liquid phase organic material. As the concentration of the dissolved disaccharide in the liquid dye concentrate becomes smaller, the benefit of the disaccharide helping to maintain the fluorogenic dyes in a non-aggregated state, in both the liquid dye concentrate and in the stained fluid sample, may decrease. In some preferred implementations, whether or not the liquid medium comprises the liquid phase organic material, liquid dye concentrate comprises a concentration of disaccharide of at least 1 weight percent, preferably at least 4 weight percent, more preferably at least 9 weight percent and even more preferably at least 12 weight percent. As the concentration of disaccharide becomes higher, fluid viscosities may become very high and the liquid dye concentrate may become difficult to handle and accurately measure for use in a staining operation. Also, at some level higher disaccharide concentrations in stained fluid samples may start to interfere with and degrade flow cytometry evaluation performance. In some preferred implementations, whether or not the liquid medium includes the liquid phase organic material, the liquid dye concentrate comprises a concentration of disaccharide of no greater than 45 percent, preferably no greater than no greater than 30 weight percent, more preferably no greater than 24 weight percent and even more preferably no greater than 20 weight percent. One preferred range for dissolved disaccharide in the liquid dye concentrate is in a range of from 9 weight percent to 24 weight percent. The disaccharide may include only a single type of disaccharide material or may include a mixture of multiple disaccharide materials. The disaccharide may include for example one or more of trehalose, sucrose, lactose, lactulose, melibiose, melibiulose, cellobiose, nigerose, isomaltose, isomaltulose, maltulose, rutinose, β-laminaribiose, or maltose, with trehalose generally being a preferred disaccharide material. As summarized in in International Patent Application No. PCT/US2019/044623, of the tested disaccharides of sucrose, lactose and trehalose reported in that reference, all significantly reduced blank particle counts on a monitored flow cytometer detection channel, with trehalose exhibiting the greatest reduction, while the tested monosaccharide galactose and the tested trisaccharides matotriose and raffinose either increased blank counts (indicating greater fluorogenic dye aggregation) or did not improve the blank counts (indicating no significant benefit from their use).

The plurality of different fluorogenic dyes in the liquid dye concentrate may include, for example, any of the fluorogenic dyes identified for use in dry powder dye compositions, which may include only two fluorogenic dyes, for example a first fluorogenic dye for nonspecific nucleic acid staining and a second fluorogenic dye for nonspecific protein staining, or may include one or more additional different fluorogenic dyes in addition to such a first fluorogenic dye and second fluorogenic dye. In some preferred implementations, the liquid dye concentrate includes only two fluorogenic dyes, a first fluorogenic dye for nonspecific nucleic acid staining and a second fluorogenic dye for nonspecific protein staining. Unless otherwise stated in the context of a particular reference, references below to a first fluorogenic dye are to a fluorogenic dye for nonspecific nucleic acid staining and references to a second fluorogenic dye are to a fluorogenic dye for nonspecific protein staining. For brevity, the plurality of different fluorogenic dyes is sometimes referred to herein as simply the fluorogenic dyes. The fluorogenic dyes are typically, and preferably, dissolved in the liquid medium.

One or more, and often all, of the fluorogenic dyes in the liquid dye concentrate may contain one or more aromatic group that contributes to the fluorogenic dye being susceptible to pi stacking interactions in aqueous liquids. Aromatic groups include a cyclic structure having one or more rings with a very stable electron shell configuration and a generally planar structure, and are generally susceptible to pi stacking interactions in aqueous liquids, although the degree of susceptibility may vary based on the particular aromatic group and the particular molecular structure in which the aromatic group is contained. Each of the fluorogenic dyes has at least one such aromatic group susceptible to pi stacking interactions in aqueous liquids. Such aromatic groups may be homocyclic, containing only carbon atoms in the aromatic ring or rings, or heterocyclic, containing one or more atoms other than carbon (referred to as heteroatoms) in the aromatic ring or rings. An aromatic ring containing only carbon atoms in the ring may be referred to as a homoaromatic ring, and an aromatic ring containing a heteroatom in the ring may be referred to as a heteroaromatic ring. Some common heteroatoms include nitrogen, oxygen and sulfur, and an aromatic group of a fluorogenic dye may include one or more of these or other heteroatoms. Such an aromatic group may often include a 6-member aromatic ring and/or a 5-member aromatic ring, each of which may independently be a homocyclic ring or a heterocyclic ring. Such an aromatic group may include a single aromatic ring or may be polycyclic, containing multiple aromatic rings in the aromatic group. Such aromatic group may be part of a fused ring moiety, for example including a 6-member aromatic ring fused with either one or both of a 5-member aromatic ring and a 6-member aromatic ring. One important type of fused ring moiety used in fluorogenic dyes includes a 6-member homoaromatic ring fused with a 6-member heteroaromatic ring, for example including nitrogen as a heteroatom. Another important type of fused ring moiety used in fluorogenic dyes includes 6-member homoaromatic ring fused with a 5-member heteroaromatic ring, and in which the heteroaromatic ring includes both nitrogen and oxygen as heteroatoms or both nitrogen and sulfur as heteroatoms. Examples of some fluorogenic dyes having such fused ring moieties are described for example in U.S. Pat. Nos. 5,410,030 and 5,616,502; each and every part of which is incorporated herein by reference in their entireties.

Many useful fluorogenic dyes for use with the aspects of this disclosure are cyanine dyes, and one or more of the fluorogenic dyes may be a cyanine dye. Cyanine dyes are those including methine group (=CH—) linkages. One important group of cyanine dyes are referred to as merocyanine dyes, which have a quaternary nitrogen heterocycle linked to an electron pair-donating moiety by an alkylene or polyalkylene bridge. The fluorogenic dyes disclosed in U.S. Pat. Nos. 5,410,030 and 5,616,502 are examples of cyanine dyes, with those of U.S. Pat. No. 5,616,502 being examples of merocyanine dyes. The cyanine dyes disclosed in U.S. Pat. No. 5,410,030 are cyanine dimers, and more particularly certain dimers of unsymmetrical cyanine dyes. One or more of, or all of, the plurality of different fluorogenic dyes may be cyanine dyes, and may be cyanine dyes as disclosed in U.S. Pat. Nos. 5,410,030 and 5,616,502.

In some preferred implementations, the first fluorogenic dye is for nonspecific nucleic acid staining. In some preferred implementations, the second fluorogenic dye is for nonspecific protein staining. In some particularly preferred implementations, the first fluorogenic dye is for nonspecific nucleic acid staining and the second fluorogenic dye is for nonspecific protein staining. Preferably, the first fluorogenic dye for nonspecific nucleic acid staining and the second fluorogenic dye for nonspecific protein staining are each cyanine dyes, and more preferably with the second fluorogenic dye being a merocyanine dye.

One specific example of a fluorogenic dye for nonspecific nucleic acid staining, which may be used as the first fluorogenic dye, is POPO™-3 iodide nucleic acid stain (ThermoFisher Scientific), which is a cyanine dimer of a type as disclosed in U.S. Pat. No. 5,410,030, and which has been reported to have the following chemical formula (e.g., at www.thermofisher.com/order/catalog/product/P3584):

ent fluorogenic dyes in a liquid medium, each different said fluorogenic dye having a different fluorescent emission signature for detection when bound to a said unassociated virus-size particle; and an aqueous sample dilution liquid for preparing aqueous diluted fluid samples containing biological material for flow cytometry evaluation for unassociated virus-size particles, the aqueous sample dilution liquid being contained in a scaled second container;

and wherein the liquid dye concentrate comprises at least one member selected from the group consisting of:
(i) the liquid medium comprises a liquid mixture including water and liquid phase organic material;
(ii) disaccharide dissolved in the liquid medium; and
(iii) a combination including both (i) and (ii).

A number of feature refinements and additional features are applicable to this second aspect of the disclosure. These feature refinements and additional features may be used individually or in any combination within the subject matter of this aspect or any other aspect of this disclosure. As such, each of the following features may, but are not required to be, used with any other feature or a combination of features of this aspect or any other aspect of this disclosure.

The liquid dye concentrate may be or have features as described with respect to the first aspect. The sealed first container with the liquid dye concentrate may the in the form of the fluorescent stain product of the first aspect.

A third aspect of this disclosure is directed to a method flow cytometry evaluation of biological material for unassociated virus-size particles, the method comprising:

providing an aqueous preliminary fluid sample with biological material in an aqueous liquid for flow cytometry evaluation for unassociated virus-size particles;

providing a liquid dye concentrate comprising a plurality of different fluorogenic dyes in a liquid medium, each different said fluorogenic dye having a different fluorescent emission signature for detection when bound to a said unassociated virus-size particle;

preparing an aqueous stained fluid sample, comprising staining the preliminary fluid sample with liquid dye concentrate;

subjecting the stained fluid sample to flow cytometry in a flow cytometer to detect and count occurrences of the unassociated virus-size particles stained with at least one of the fluorogenic dyes;

and wherein the method comprises at least one member selected from the group consisting of
(i) the liquid medium comprises a liquid mixture including water and liquid phase organic material;
(ii) the liquid dye concentrate comprising disaccharide dissolved in the liquid medium;
(iii) the providing the liquid dye concentrate being in the absence of reconstituting the fluorogenic dyes from a dry form into the liquid medium; and One specific example of a fluorogenic dye for nonspecific protein staining, which may be used as the second fluorogenic dye, is SYPRO™ red protein stain (ThermoFisher Scientific), which is a merocyanine dye of a type as disclosed in U.S. Pat. No. 5,616,502, and which has been reported to be based on the following chemical formula (e.g., at de.wikipedia.org/wiki/SYPRO_Red#cite_note-emchenko-1):

where m is 5 or 6 and n is an integer from 2 to 4.

Some other example fluorogenic dyes for use with the different aspects of this disclosure include: YOYO™-1 iodide nucleic acid stain (ThermoFisher Scientific), YO-PRO™-1 iodide nucleic acid stain (ThermoFisher Scientific), SYPRO™ Tangerine protein stain (ThermoFisher Scientific), Krypton™ protein stain (ThermoFisher Scientific), and SYBR™ Green nucleic acid stains such as SYBR™ Green I and SYBR™ Green II (ThermoFisher Scientific).

A second aspect of this disclosure is directed to a kit for preparing fluorescently stained fluid samples containing biological material for flow cytometry evaluation for unassociated virus-size particles, the kit comprising:

a liquid dye concentrate in a sealed first container, the liquid dye concentrate comprising a plurality of differ- (iv) combinations including two or more of any of (i)-(iii).

A number of feature refinements and additional features are applicable to this third aspect of the disclosure. These feature refinements and additional features may be used individually or in any combination within the subject matter of this aspect or any other aspect of this disclosure. As such, each of the following features may, but are not required to be, used with any other feature or a combination of features of this aspect or any other aspect of this disclosure.

The liquid dye concentrate may be or have features as described with respect to the first aspect. The sealed first container with the liquid dye concentrate may the in the form of the fluorescent stain product of the first aspect or in the kit of the second aspect. The providing the liquid dye concentrate may include unsealing such a first sealed container and removing the liquid dye concentrate, or a portion thereof, from the unsealed first container. The providing an aqueous preliminary fluid sample may include diluting the prior formulation including the biological material with aqueous sample dilution liquid, for example which may be provided in the kit of the second aspect.

In some implementations, preparing the stained fluid sample may include mixing at least a portion of the liquid dye concentrate directly with a preliminary fluid sample containing the biological material of interest for evaluation to prepare a stained fluid sample for flow cytometry evaluation of the dissolved disaccharide in the stained fluid sample.

Each of the plurality of different fluorogenic dyes may be included in the liquid dye concentrate in such amounts so as to provide a desired concentration for each such fluorogenic dye in the concentrated dye formulation, and ultimately in the stained fluid sample for flow cytometry evaluation. In terms of molar concentration, the liquid dye concentrate may be prepared such that each of the plurality of different fluorogenic dyes (including each of the first fluorogenic dye in the second fluorogenic dye) may independently have a concentration within a range having a lower limit selected from the group consisting of 1 micromole per liter, 10 micromoles per liter, 100 micromoles per liter and 1000 micromoles per liter and an upper limit selected from the group consisting of 35,000 micromoles per liter, 25,000 micromoles per liter, 20,000 micromoles per liter and 15,000 micromoles per liter. In terms of weight-to-volume concentration, the liquid dye concentrate may be prepared such that each of the plurality of different fluorogenic dyes (including each of the first fluorogenic dye and the second fluorogenic dye) may independently have a concentration within a range having a lower limit and selected from the group consisting of 10 micrograms per milliliter, 100 micrograms per milliliter and 500 micrograms per milliliter and an upper limit selected from the group consisting of 15,000 micrograms per milliliter, 7,000 micrograms per milliliter and 3,500 micrograms per milliliter.

The flow cytometer may be any flow cytometer configured to evaluate for virus-size particles through detection and analysis of fluorescent emission responses of the plurality of fluorogenic dyes. The flow cytometer may be of a type in which the stained fluid sample flows through the flow cell of the flow cytometer without hydrodynamically focusing the stained fluid sample with a sheath fluid. In preferred implementations, however, the flow cytometer is of a type in which the stained fluid sample is hydrodynamically focused with a sheath fluid introduced around the flowing fluid sample prior to introduction of the stained fluid sample into the flow cell of the flow cytometer. In the flow cell, the stained fluid sample, preferably in a hydrodynamically focused state, is subjected to one or more stimuli to stimulate a fluorescent emission response from each fluorogenic dye (including the first fluorogenic dye in the second fluorogenic dye) when attached to an unassociated virus-size particle stained with such fluorogenic dye, and detecting for the fluorescent emission signature of each of the plurality of fluorogenic dyes. The one or more stimuli to which the stained fluid sample is subjected in the flow cell may preferably include at least one excitation radiation. Such an excitation radiation may be of a wavelength range sufficient to stimulate the fluorescent emission response from at least one and optionally multiple ones of the plurality of fluorogenic dyes when attached to virus-size particle. The one or more stimuli may include multiple different excitation radiations having different wavelength ranges for stimulating fluorescent emission responses from different ones of the plurality of fluorogenic dyes. In preferred flow cytometry processing, the flow rate of the stained fluid sample, and preferably in a hydrodynamically focused state, through the flow cell is maintained at a very low flow rate to enhance accurate detection of stained virus-size particles, and preferably such flow rate of the stained fluid sample through the flow cell is in a range having a lower limit of 300 nanoliters per minute, 600 nanoliters per minute or 800 nanoliters per minute and an upper limit of 6000 nanoliters per minute, 3000 nanoliters per minute or 2000 nanoliters per minute, more preferably in a range of from 600 nanoliters per minute to 3000 nanoliters per minute and even more preferably in a range of from 600 nanoliters per minute to 2000 nanoliters per minute. The flow cytometry preferably comprises separately detecting for each of the plurality of different fluorescent emission signatures of the plurality of different fluorogenic dyes, and time correlating detection of at least one such fluorescent emission signature (e.g., of the first fluorogenic dye) and detection of at least one other such fluorescent emission signature (e.g., of the second fluorogenic dye) to determine a detection event indicative of an occurrence of passage through the flow cell of an unassociated virus-size particle stained with each of the time different fluorogenic dyes for which fluorescent emission signatures are time correlated (e.g., a virus-size particle stained with both the first fluorogenic dye and the second fluorogenic dye). Such a time correlation may also be used to identify an occurrence of a virus-size particle passing through the flow cell that is stained with one of the plurality of fluorogenic dyes (e.g., stained with the second fluorogenic dye) and not another one of the plurality of fluorogenic dyes (e.g., not stained with the first fluorogenic dye), for example to identify a virus-size particles with an attached fluorogenic dye non-specifically bound to protein content and not having attached to it another fluorogenic dye for non-specific staining of nucleic acid content, indicative of a particle containing protein and not containing genetic material. One preferred flow cytometer configured for flow cytometry evaluation of fluorescently stained virus-size particles is the Virus Counter® 3100 flow cytometer.

A fourth aspect of this disclosure is directed to a stained fluid sample for flow cytometry evaluation for unassociated virus-size particles, the stained fluid sample comprising:
  an aqueous liquid medium;
  a biological material of interest for flow cytometry evaluation for the unassociated virus-size particles dispersed in the aqueous liquid medium; and
  a plurality of different fluorogenic dyes dispersed in the aqueous liquid medium, each said fluorogenic dye having a different fluorescent emission signature for detection when bound to a said unassociated virus-size particle;

and wherein:

the aqueous liquid medium comprises an liquid organic phase material at a concentration in a range of from 0.25 weight percent to 2 weight percent; and the stained fluid sample comprises a disaccharide at a concentration of the disaccharide in a range of from 0.1 weight percent to 3 weight percent dissolved in the aqueous liquid medium.

A number of feature refinements and additional features are applicable to this fourth aspect of the disclosure. These feature refinements and additional features may be used individually or in any combination within the subject matter of this aspect or any other aspect of this disclosure. As such, each of the following features may, but are not required to be, used with any other feature or a combination of features of this aspect or any other aspect of this disclosure.

The stained fluid sample of the fourth aspect may be or have any feature or features of a stained fluid sample described with respect to the method of the third aspect of this disclosure. The fluorogenic dyes may be or have any features discussed with respect to the product of the first aspect, the kit of the second aspect or the method of the third aspect.

Numerous additional features and advantages of the present disclosure will become apparent to those skilled in the art upon consideration of the embodiment descriptions, including the in the numbered example implementation combinations, provided hereinbelow and in the appended claims.

DETAILED DESCRIPTION

Figure 1:
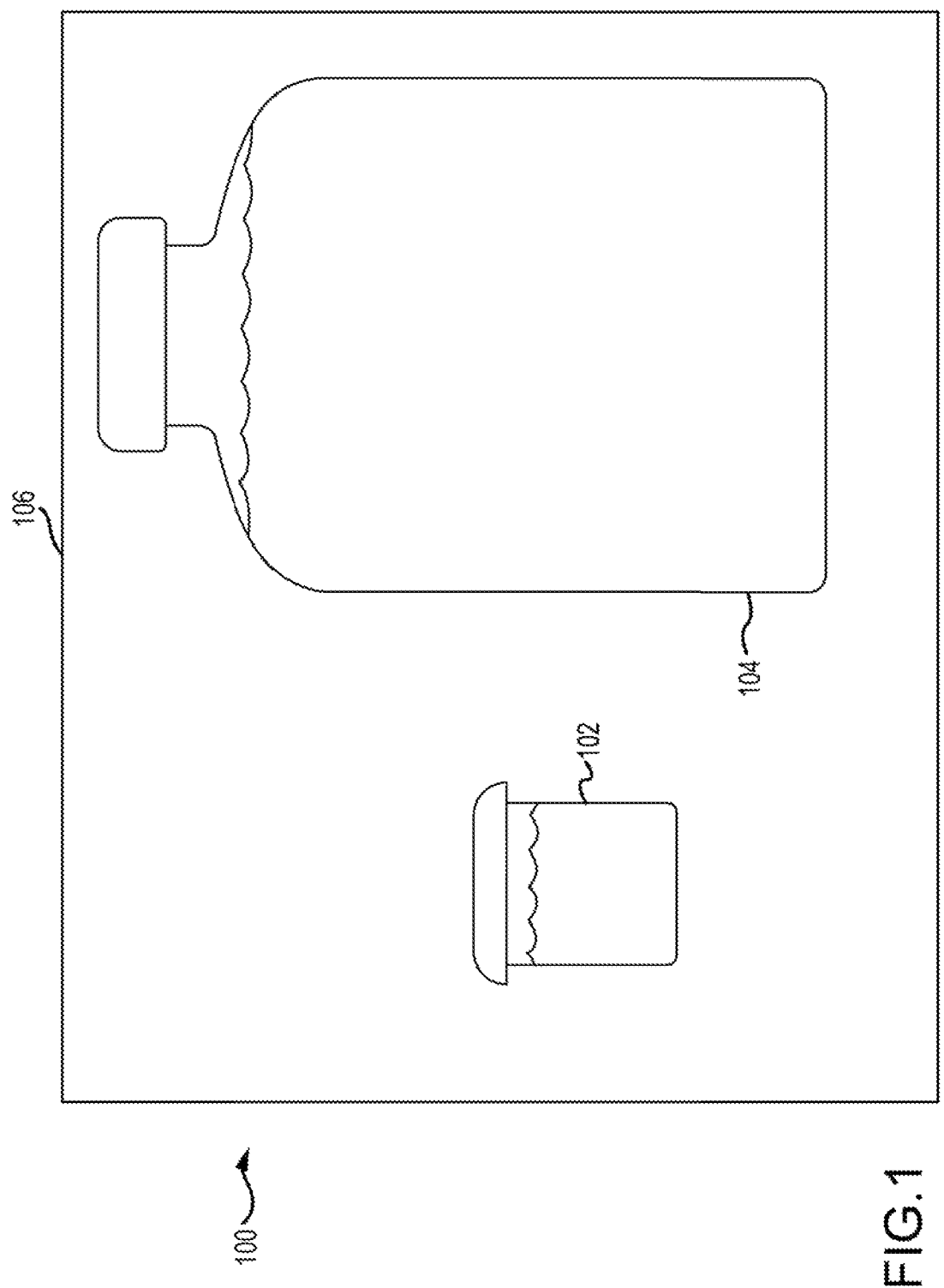
FIG. 1 illustrates an embodiment of a kit of this disclosure for fluorescent staining unassociated virus-size particles with multiple fluorogenic dyes for flow cytometry evaluation for the unassociated virus-size particles.

Reference is made to FIG. 1, which illustrates an example embodiment of a kit 100 including a first sealed container 102, in the form of a capped bottle, containing a liquid dye concentrate including a mixture of a plurality of different fluorogenic dyes each having a different fluorescent emission signature and each containing at least one aromatic group susceptible to pi stacking interactions in aqueous liquid media. The first sealed container 102 may include a quantity of the liquid dye concentrate to prepare many stained fluid samples for flow cytometry evaluation. The liquid dye concentrate and fluorogenic dyes in the dry powder composition may have any or any combination of the features as described elsewhere herein. As shown in FIG. 1, the kit 100 includes a second sealed container 104 in the form of a capped bottle containing aqueous sample dilution liquid (e.g., an aqueous buffered solution) for use to dilute biological material into diluted fluid samples for flow cytometry evaluation. The kit 1 includes the first sealed container 102 and the second sealed container 104 packaged together in a common packaging enclosure 106, for example a common packaging box or bag. In alternative implementations, the kit 100 may include within the common packaging enclosure 106 one or more components in addition to those illustrated in FIG. 1. With continued reference to FIG. 1, when the stained fluid sample to be prepared with the kit 100 is to include dissolved disaccharide, some or all of such disaccharide may be included in the liquid dye concentrate (preferably) in the first sealed container 102 and/or in the aqueous sample dilution liquid in the second sealed container 104.

Figure 2:
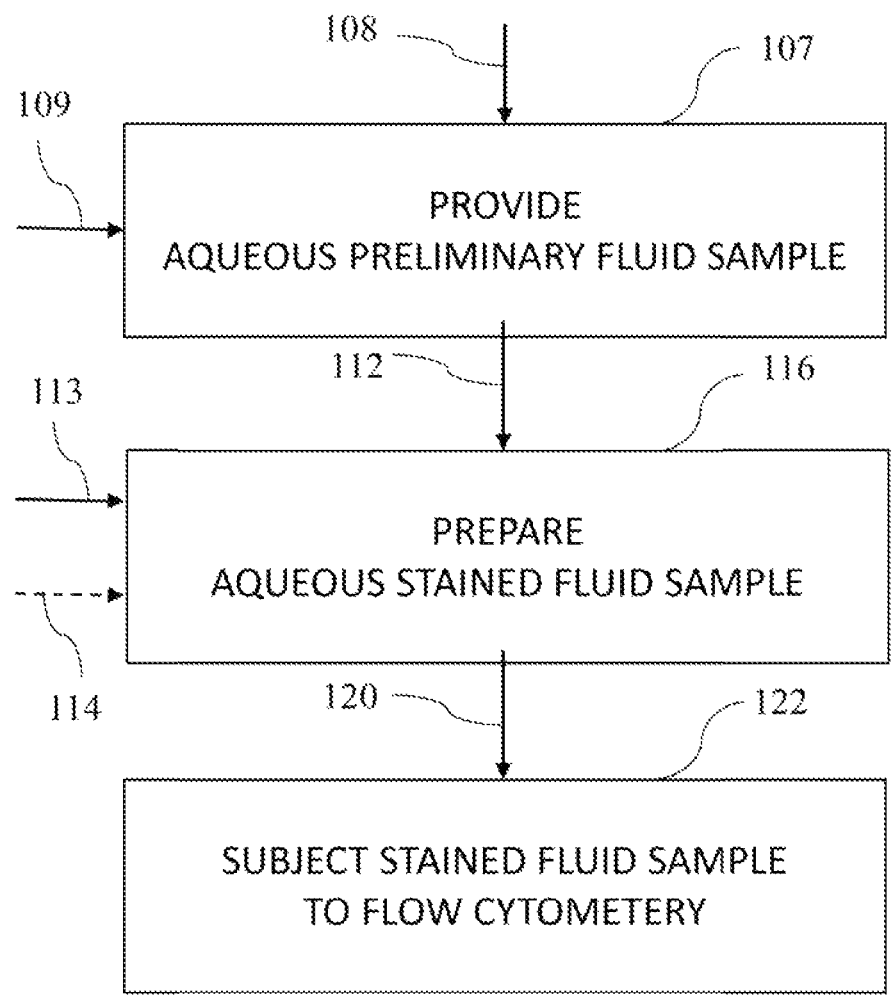
FIG. 2 is a generalized process block diagram illustrating an embodiment of a method of this disclosure for flow cytometry evaluation of a fluid sample for unassociated virus-size particles stained with multiple fluorogenic dyes susceptible to pi stacking interactions in aqueous liquid.

Reference is made to FIG. 2 with a generalized process block flow diagram illustrating one embodiment of a method of this disclosure for flow cytometry evaluation of the fluid sample for unassociated virus-size particles stained with multiple fluorogenic dyes susceptible to pi stacking in aqueous liquids. The processing illustrated in FIG. 2 includes a step 107 to prepare an aqueous preliminary fluid sample in which a sample of biological material 108 is diluted to a desired dilution ratio with aqueous sample dilution liquid 109. As may be appreciated, the sample of biological material 108 as provided to the step 107 may already be in a first diluted fluid sample at a first dilution ratio and in the step 107 the fluid sample is further diluted to higher dilution ratio. In that respect, the resulting preliminary fluid sample 112 may be one diluted sample in a series of diluted samples at different dilution ratios. The preliminary fluid sample 112 is then subjected to a step 116 to prepare an aqueous stained fluid sample, during which a liquid dye concentrate 113, including a plurality of different fluorogenic dyes as disclosed herein, is added to the preliminary fluid sample 112 as part of a staining operation to prepare a stained fluid sample 120. Also shown in step 116 is an optional staining of the preliminary fluid sample 112 with a fluorophore stain 114. Such a fluorophore stain 114 may, for example, be a fluorescent antibody stain with a fluorescent stain molecule conjugated to an antibody specific for binding to a targeted epitope on a targeted virus-size particle. Such a fluorescent antibody stain may be, for example, of a type as disclosed in U.S. patent application Ser. No. 15/558,107, now issued as U.S. Pat. No. 10,161, 850, and the corresponding U.S. patent application publication US 2018/0052163 A1, the entire contents of each of which are is incorporated herein by reference for all purposes. Such a fluorescent antibody stain may have an emission response signature different than each of the fluorogenic dyes, and may be detected on a separate photodetection channel of the flow cytometer.

In the general processing illustrated in FIG. 2, the stained fluid sample 120, including at least the plurality of fluorogenic dyes from the liquid dye concentrate 113, is subjected to flow cytometry in step 122. During the step 122, the stained fluid sample 120 is introduced into and processed through a flow cytometer for flow cytometry evaluation for presence of targeted unassociated virus-size particles, and to detect and count occurrences at least of unassociated virus-size particles stained with multiple fluorogenic dyes (e.g., a first fluorogenic dye for non-specific nucleic acid staining and a second fluorogenic dye for non-specific protein staining). During the flow cytometry evaluation, a controlled flow of the stained fluid sample 120 is subjected in a flow cell of the flow cytometer to one or more excitation stimuli, such as light from one or more lasers, to cause the respective fluorescent emission response from each fluorogenic dye with which a particle passing through the flow cytometer is stained. Light coming from the flow cell is detected by one or more light detector to identify the presence of a fluorescent emission response from each such fluorogenic dye. Simultaneous detection of multiple different fluorescent emission responses indicates passage of a particle stained with the multiple different fluorogenic dyes and such a simultaneous detection may be counted as an occurrence of a virus-size particle stained with properties indicated by such multiple fluorogenic dyes. The fluorescent emission responses of the fluorogenic dyes may be detected separately by separate photodetectors each configured for detection of the specific fluorescent emission signature of the targeted fluorogenic dye. Detected fluorescent emission signatures may be processed by a data analysis system to identify detection events indicative of a virus-size particle stained with the respective fluorogenic dye and to count and determine a concentration of such virus-size particles. When the stained fluid sample 120 includes the fluorophore stain 114, the flow cytometry may also include separately detecting for the fluorescent emission signature of the fluorophore stain 114 bound to a virus-size particle, and may be correlated with detection of the fluorescent emission signatures to identify particular particle attributes of a detected virus-size particle, for example a particular epitope on the virus-size particle corresponding to an antibody of a fluorescent antibody stain.

With continued reference to FIG. 2, when the stained fluid sample 120 is prepared containing dissolved disaccharide, some or all of the disaccharide may be included in the aqueous sample dilution liquid 109 and/or in the liquid dye concentrate 113. In one variation of the processing shown in FIG. 2 when the stained fluid sample 120 includes dissolved disaccharide, at least a portion, and preferably all of the disaccharide, in the stained fluid sample is provided in the liquid dye concentrate 113. When the stained fluid sample 120 includes a liquid phase organic material, preferably DMSO, in preferred processing at least a portion of the liquid phase organic material, and more preferably all or substantially all of the liquid phase organic material, is provided in the liquid dye concentrate 113. In some variations, liquid phase organic material may be provided in the aqueous sample dilution liquid 109.

Figure 3:
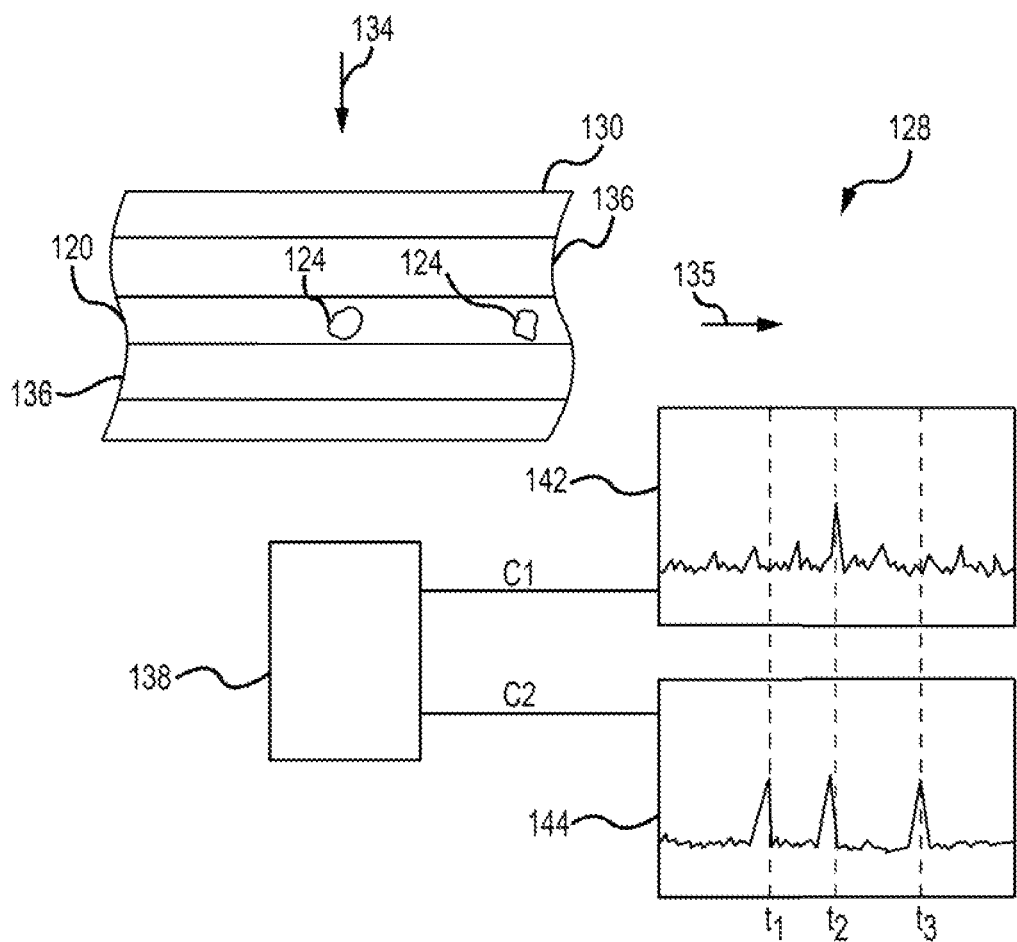
FIG. 3 illustrates an embodiment of operation of a flow cytometer for performing a flow cytometry evaluation on a stained fluid sample for virus-size particles as part of a method of this disclosure.

Reference is now made to FIG. 3, illustrating one example of detecting virus-size particles stained with multiple fluorogenic dyes during flow cytometry, for example during the processing to subject the stained fluid sample 120 to flow cytometry in step 122 illustrated in FIG. 2 and discussed above. FIG. 3 shows partial componentry of a flow cytometer 128, including a flow cell 130 and a light detection and analysis system 138. As shown in FIG. 3, a flow of such a stained fluid sample 120 through the flow cell 130 is subjected in the flow cell 130 to excitation radiation 134 from a light source (not shown) of the flow cytometer 128. Such a light source may be, for example, a laser, LED or other light source. As illustrated in FIG. 3, the stained fluid sample 120 includes virus-size particles 124, and the stained fluid sample is shown as flowing through a flow cell 130 of a flow cytometer in the direction of the flow arrow 135. In the example illustrated in FIG. 3, the stained fluid sample 120 has been hydrodynamically focused with a sheath fluid 136 prior to introduction into the flow cell 130. As illustrated in FIG. 3, the sheath fluid 136 is shown as a distinct fluid relative to the stained fluid sample 120. As may be appreciated, differentiation between such a sheath fluid 136 and stained fluid sample 120 may not be as distinct as illustrated in FIG. 3. The light detector and analysis system 138 in FIG. 3 is illustrated to include two photodetectors for separately detecting radiation wavelength ranges associated with the different fluorescent emission signatures of two different fluorogenic dyes as a consequence of excitation by the excitation radiation 134. FIG. 3 also shows a first time series plot 142 with an example output (C1) of a first photodetector detecting for fluorescent emission response from a first fluorogenic dye staining a virus-size particle 124 and a second time series plot 144 with an example output (C2) of a second photodetector detecting for fluorescent emission response from a second fluorogenic dye staining a virus-size particle 124. The time series plots 142 and 144 are plots of voltage from the respective photodetector versus time, and with the indicated voltage peaks at times t1, t2 and t3 indicating detection of such a virus-size particle 124 stained with a fluorogenic dye. In this example, a first fluorogenic dye may be a fluorogenic dye for nonspecific nucleic acid and a second fluorogenic dye may be a fluorogenic dye for nonspecific protein staining. The second time series plot 144 is illustrated with three voltage peaks at times t1, t2 and t3 indicative of the passage through the flow cell 130 of three virus-size particles 124 with the second fluorogenic dye staining protein content of such virus-size particles 124. The first time series plot 142 is illustrated with a voltage peak at time t2 indicative of the passage through the flow cell 130 of a virus-size particle 124 with the first fluorogenic dye staining nucleic acid content of such a virus-size particle 124. The coincidence at time t2 of a voltage peak on both the first time series plot 142 and the second time series plot 144 indicates passage through the flow cell 130 of a virus-size particle 124 containing both nucleic acid content and protein content, for example such as may be the case for an in-tact virus particle, or virion. The occurrence of the voltage peaks at t1 and t3 on the second time series plot 144 with no corresponding voltage peaks on the first time series plot 142 indicates passage through the flow cell of virus-size particles 124 including protein content and not including nucleic acid content, such as may be the case for a virus-like particle, exosome or particle fragment including protein content but not including genetic material. In alternative embodiments, the light detector and analysis system 138 may include photodetectors for detecting fluorescent emission signatures from more than two different fluorogenic dyes and/or to detect one or more fluorescent antibody stains indicative of the presence of a particular epitope on a targeted virus-size particle. Although the flow cytometer 128 is illustrated as including a single light source providing a single excitation radiation 134 to stimulate multiple different fluorescent emission responses from different fluorogenic dyes, such a flow cytometer 128 may include multiple different light sources each providing a different excitation radiation in a different wavelength range where the fluorescent emission responses from different fluorogenic dyes and/or antibody stains are stimulated by different excitation radiation wavelength ranges. Also, although processing in FIG. 3 is shown using a hydrodynamically focused stained fluid sample 120, such a stained fluid 120 may alternatively be processed through a flow cytometer in which samples are not hydrodynamically focused, although hydrodynamically focused systems are preferred. In a preferred operation, a flow rate of the hydrodynamically focused stained fluid sample 120 through the flow cell 130 may be very low, preferably 6000 nanoliters per minute or lower, more preferably 3000 nanoliters per minute or lower, more preferably in a range having a lower limit of 300 nanoliters per minute, 600 nanoliters per minute or 800 nanoliters per minute and an upper limit of 6000 nanoliters per minute, 3000 nanoliters per minute or 2000 nanoliters per minute, which range is preferably from 600 nanoliters per minute to 3000 nanoliters per minute and is even more preferably from 600 nanoliters per minute to 2000 nanoliters per minute.

EXEMPLARY IMPLEMENTATION COMBINATIONS

Some other contemplated embodiments of implementation combinations for various aspects of this disclosure, with or without additional features as disclosed above or elsewhere herein, are summarized in the numbered example combinations presented below, and in the appended claims:

1. A kit for preparing fluorescently stained fluid samples containing biological material for flow cytometry evaluation for unassociated virus-size particles, the kit comprising:
  a liquid dye concentrate in a sealed first container, the liquid dye concentrate comprising a plurality of different fluorogenic dyes in a liquid medium, each different said fluorogenic dye having a different fluorescent emission signature for detection when bound to a said unassociated virus-size particle; and
  an aqueous sample dilution liquid for preparing aqueous diluted fluid samples containing biological material for flow cytometry evaluation for unassociated virus-size particles, the aqueous sample dilution liquid being contained in a sealed second container;
  and wherein the liquid dye concentrate comprises at least one member selected from the group consisting of:
    (i) the liquid medium comprises a liquid mixture including water and liquid phase organic material, and preferably the liquid medium is aqueous, and more preferably the liquid medium comprises more than 50 percent by moles of water;
    (ii) disaccharide dissolved in the liquid medium; and
    (iii) a combination including both (i) and (ii).

2. The kit of combination 1, wherein the sealed first container and the sealed second container are packaged together within a common packaging enclosure.

3. The kit of combination 2, wherein the common packaging enclosure comprises a sealed plastic bag.

4. The kit of any one of combinations 1-3, wherein the aqueous dilution liquid comprises an aqueous buffer solution.

5. A fluorescent stain product with multiple fluorogenic dyes for direct fluorescent staining of aqueous fluid samples containing biological materials with multiple fluorogenic dyes for flow cytometry evaluation of stained fluid samples for unassociated virus-size particles, the fluorescent stain product comprising:
  a liquid dye concentrate comprising a plurality of different fluorogenic dyes in a liquid medium, each different said fluorogenic dye having a different fluorescent emission signature for detection when bound to a said unassociated virus-size particle; and
  a sealed container containing the liquid dye concentrate;
  and wherein the liquid dye concentrate comprises at least one member selected from the group consisting of:
    (i) the liquid medium comprises a mixture including water and liquid phase organic material, and preferably the liquid medium is aqueous, and more preferably the liquid medium comprises more than 50 percent by moles of water;
    (ii) disaccharide dissolved in the liquid medium; and
    (iii) a combination including both (i) and (ii).

6. The kit of any one of combinations 1-4, wherein the sealed first container containing the liquid dye concentrate is in the form of the fluorescent stain product of combination 5.

7. A method for flow cytometry evaluation of biological material for unassociated virus-size particles, the method comprising:
  providing an aqueous preliminary fluid sample with biological material in an aqueous liquid for flow cytometry evaluation for unassociated virus-size particles;
  providing a liquid dye concentrate comprising a plurality of different fluorogenic dyes in a liquid medium, each different said fluorogenic dye having a different fluorescent emission signature for detection when bound to a said unassociated virus-size particle;
  preparing an aqueous stained fluid sample, comprising staining the preliminary fluid sample with liquid dye concentrate;
  subjecting the stained fluid sample to flow cytometry in a flow cytometer to detect and count occurrences of the unassociated virus-size particles stained with at least one of the fluorogenic dyes;
  and wherein the method comprises at least one member selected from the group consisting of:
    (i) the liquid medium comprising a mixture including water and liquid phase organic material, and preferably the liquid medium is aqueous, and more preferably the liquid medium comprises more than 50 percent by moles of water;
    (ii) the liquid dye concentrate comprising disaccharide dissolved in the liquid medium;
    (iii) the providing the liquid dye concentrate being in the absence of reconstituting the fluorogenic dyes from a dry form into the liquid medium; and
    (iv) combinations including two or more of any of (i)-(iii).

8. The method of combination 7, wherein the staining the preliminary fluid sample comprises combining the preliminary fluid sample and the liquid dye concentrate at a volume ratio of volume of the liquid dye concentrate to volume of the preliminary fluid sample of at least 1:125.

9. The method of either one of combination 7 or combination 8, wherein the staining the preliminary fluid sample comprises combining the preliminary fluid sample with a volume of the liquid dye concentrate in a volume ratio of the volume of the liquid dye concentrate to a volume of the preliminary fluid sample of no greater than 1:24.

10. The method of any one of combinations 7-9, comprising the providing the liquid dye concentrate being in the absence of reconstituting the fluorogenic dyes from a dry form into the liquid medium.

11. The method of any one of combinations 7-10, wherein the providing the liquid dye concentrate comprises unsealing a sealed container containing the liquid dye concentrate and removing from the unsealed container a quantity of the liquid dye concentrate for combining with the preliminary fluid sample during the staining.

12. The method of combination 11, wherein the sealed container containing the liquid dye concentrate is a said sealed container of the fluorescent stain product of combination 5.

13. The method of combination 11, wherein the sealed container containing the liquid dye concentrate is a said sealed first container of the kit of any one of combinations 1-4 and 6.

14. The method of combination 13, wherein the providing the preliminary fluid sample comprises unsealing a said sealed second container of the kit of any one of combinations 1-4 and 6 and diluting a biological material with a quantity of the aqueous sample dilution liquid removed from the unsealed second container.

15. The method of combination 14, comprising:
providing a plurality of said preliminary fluid samples each with a portion of a biological material from a stock source and each diluted to different dilution ratios with the aqueous sample dilution liquid;
and separately subjecting each said stained fluid sample to the flow cytometry.

16. The method of either one of combination 14 or combination 15, wherein the sealed first container and the sealed second container of the kit are packaged together within the common packaging enclosure of either one of combination 2 or combination 3, and the method comprises removing the first sealed container and the second sealed container from the common packaging enclosure.

17. The method of any one of combinations 7-16, wherein the stained fluid sample comprises a concentration of the liquid phase organic material of at least 0.25 weight percent, optionally at least 0.35 weight percent or optionally at least 0.5 weight percent.

18. The method of any one of combinations 7-17, wherein the stained fluid sample comprises a concentration of the liquid phase organic material of no larger than 2 weight percent, optionally no larger than 2 weight percent, optionally no larger than 1.25 weight percent or optionally no larger than 0.75 weight percent; and with one preferred range for the concentration of the liquid phase organic material being from 0.25 weight percent to 1.25 weight percent and a more preferred range being from 0.5 weight percent to 1.25 weight percent.

19. The method of any one of combinations 7-18, wherein the stained fluid sample comprises a concentration of the disaccharide of at least 0.1 weight percent, optionally at least 0.2 weight percent or optionally at least 0.3 weight percent.

20. The method of any one of combinations 7-19, wherein the stained fluid sample comprises a concentration of the disaccharide of no larger than 3 weight percent, optionally no larger than 2 weight percent, optionally no larger than 1 weight percent or optionally no larger than 0.75 weight percent; and with one preferred range for the concentration for the concentration of the disaccharide being from 0.1 weight percent to 2 weight percent and a more preferred range being from 0.2 weight percent to 1 weight percent.

21. The method of any one of combinations 7-20, wherein the flow cytometry comprises:
hydrodynamically focusing a flow of the stained fluid sample with a sheath fluid; and
flowing the hydrodynamically focused stained fluid sample through a flow cell in which the flowing hydrodynamically focused stained fluid sample is subjected to excitation radiation to stimulate a fluorescent emission response from each of a first said fluorogenic dye and a second said fluorogenic dye on the unassociated virus-size particles stained with both the first fluorogenic dye and the second fluorogenic dye; and
detecting for both a first fluorescent emission signature of the first said fluorogenic stain staining a said unassociated virus-size particle and a second fluorescent emission signature of the second said fluorogenic stain staining a said unassociated virus-size particle; and
wherein, the flowing comprises maintaining a flow rate of the hydrodynamically focused stained fluid sample through the flow cell in a range having a lower limit of 300 nanoliters per minute, 600 nanoliters per minute or 800 nanoliters per minute and an upper limit of 6000 nanoliters per minute, 3000 nanoliters per minute or 2000 nanoliters per minute, and preferably in a range of from 600 nanoliters per minute to 3000 nanoliters per minute.

22. The method of combination 21, wherein the flow cytometry comprises separately detecting for each of the first fluorescent emission signature and the second fluorescent emission signature and time correlating detection of the first fluorescent emission signature and detection of the second fluorescent emission signature to determine a detection event indicative of an occurrence of a said unassociated virus-size particle stained with both the first fluorogenic dye and the second fluorogenic dye.

23. The method of combination 22, wherein the flow cytometry comprises subjecting the focused stained fluid sample to a single excitation radiation source that stimulates simultaneous fluorescent emission responses from both the first fluorogenic dye and the second fluorogenic dye on a said unassociated virus-size particle stained with both the first fluorogenic dye and the second fluorogenic dye.

24. The method of combination 22, wherein the flow cytometry comprises;
subjecting the focused stained fluid sample to a first excitation radiation source that stimulates a fluorescent emission response from the first fluorogenic dye on a said unassociated virus-size particle stained with both the first fluorogenic dye and the second fluorogenic dye; and
subjecting the focused stained fluid sample to a second excitation radiation source, different than the first excitation radiation source, that stimulates a fluorescent emission response from the second fluorogenic dye on a said unassociated virus-size particle stained with both the first fluorogenic dye and the second fluorogenic dye.

25. The method of any one of combinations 7-22, wherein the preparing stained aqueous fluid sample comprises staining the preliminary fluid sample with a fluorescent antibody stain for binding with an epitope of the unassociated virus-size particle, wherein the fluorescent antibody stain has a different fluorescent emission signature than a fluorescent emission signature of each said fluorogenic dye when bound to a said unassociated virus-size particle.

26. The method of combination 25, comprising staining the preliminary fluid sample with the fluorescent antibody stain after staining the preliminary fluid sample with the liquid dye concentrate.

27. The method of combination 25, comprising staining the preliminary fluid sample with the fluorescent antibody stain prior to staining the preliminary fluid sample with the liquid dye concentrate.

28. The method of any one of combinations 25-27, wherein the preparing the stained fluid sample comprises:
mixing the fluorescent antibody stain with the biological material in the preliminary fluid sample; and
after the mixing not separating an unbound portion of the fluorescent antibody stain from the biological material prior to the flow cytometry evaluation, wherein the fluorescently-stained fluid sample as subjected to flow cytometry comprises the unbound portion of the fluorescent antibody stain.

29. The method of any one of combinations 25-28, wherein:
the stained fluid sample as fed to the flow cytometer includes the unbound portion of the fluorescent antibody stain at a concentration within a range having a lower limit and an upper limit;
the lower limit is 0.25 microgram per milliliter, optionally 0.35 microgram per milliliter, as further optionally 0.5 microgram per milliliter, further optionally 0.75 microgram per milliliter, further optionally 1 microgram per milliliter and further optionally 1.5 micrograms per milliliter; and the upper limit is 10 micrograms per milliliter, optionally 8 micrograms per milliliter, further optionally 6 micrograms per milliliter, further optionally 5 micrograms per milliliter, further optionally 4 micrograms per milliliter and further optionally 3 micrograms per milliliter.

30. The method of any one of combinations 25-29, wherein the fluorescently-stained fluid sample as fed to the flow cytometer includes a primary antibody for binding with the epitope, and wherein the fluorescent antibody stain comprises a secondary antibody with fluorophore to bind with the primary antibody to indirectly fluorescently stain the unassociated non-enveloped viral particles.

31. The method of any one of combinations 7-30, wherein the flow cytometry comprises evaluating only through detection of fluorescent emission response to identify occurrences of the unassociated virus-size particles, and not including through detection of light scatter.

32. The kit, product or method of any one of combinations 1-31, wherein the liquid medium comprises the liquid mixture including water and liquid organic phase material.

33. The kit, product or method of combination 32, wherein the liquid medium is an aqueous liquid medium comprising a major proportion on a molar basis of water and a minor proportion on a molar basis of the liquid phase organic material in the liquid mixture.

34. The kit, product or method of either one of combination 32 or combination 33, wherein the liquid mixture is a single liquid phase comprised of mutually soluble liquid components.

35. The kit, product or method of any one of combinations 32-34, wherein the liquid phase organic material comprises dimethyl sulfoxide (DMSO).

36. The kit, product or method of combination 35, wherein the liquid phase organic material consists essentially of only DMSO.

37. The kit, product or method of any one of combinations 32-35, wherein the liquid phase organic material comprises acetonitrile.

38. The kit, product or method of any one of combinations 32-37, wherein the liquid medium comprises at least 10 weight percent of the liquid phase organic material, optionally at least weight percent of the liquid phase organic material or optionally at least 20 weight percent of the liquid phase organic material.

39. The kit, product or method of any one of combinations 32-38, wherein the liquid medium comprises no greater than 50 weight percent of the liquid phase organic material, optionally no greater than 35 weight percent of the liquid phase organic material or optionally no greater than 30 weight percent of the liquid phase organic material.

40. The kit, product or method of any one of combinations 32-39, wherein the liquid medium comprises at least 50 weight percent water, optionally at least 60 weight percent water, optionally at least 65 weight percent water and optionally at least 70 weight percent water.

41. The kit, product or method of any one of combinations 32-40, wherein the liquid medium comprises no greater than 90 weight percent water.

42. The kit, product or method of any one of combinations 1-41, wherein the liquid dye concentrate comprises the disaccharide dissolved in the liquid medium.

43. The kit, product or method of combination 42, wherein the disaccharide comprises one or more than one member selected from the group consisting of trehalose, sucrose, lactose, lactulose, melibiose, melibiulose, cellobiose, nigerose, isomaltose, isomaltulose, maltulose, rutinose, β-laminaribiose, and maltose.

44. The kit, product or method of either one of combination 42 or combination 43, wherein the disaccharide comprises trehalose.

45. The kit, product or method of combination 44, wherein the disaccharide consists essentially of only trehalose.

46. The kit, product or method of any one of combinations 42-45, wherein a concentration of the disaccharide in the liquid dye concentrate is at least 1 weight percent, optionally at least 2 weight percent, further optionally at least 3 weight percent, further optionally at least 4 weight percent, further optionally at least 6 weight percent, further optionally at least 9 weight percent or further optionally at least 12 weight percent.

47. The kit, product or method of any one of combinations 42-46, wherein the concentration of the disaccharide in the liquid dye concentrate is no greater than 45 weight percent, optionally no greater than 36 weight percent, further optionally no greater than 30 weight percent, further optionally no greater than 24 weight percent, further optionally no greater than 15 weight percent, further optionally no greater than 10 weight percent or further optionally no greater than 8 weight percent.

48. A stained fluid sample for flow cytometry evaluation for unassociated virus-size particles, the stained fluid sample comprising:

an aqueous liquid medium;

a biological material of interest for flow cytometry evaluation for the unassociated virus-size particles dispersed in the aqueous liquid medium; and a plurality of different fluorogenic dyes dispersed in the aqueous liquid medium, each said fluorogenic dye having a different fluorescent emission signature for detection when bound to a said unassociated virus-size particle;

and wherein:

the aqueous liquid medium comprises a liquid organic material at a concentration in a range having a lower limit selected from the group consisting of 0.25 weight percent, 0.35 weight percent and 0.5 weight percent and an upper limit selected from the group consisting of 2 weight percent, 1.25 weight percent and 0.75 weight percent; and with one preferred range being from 0.25 weight percent to 1.25 weight percent and a more preferred range being from 0.5 weight percent to 1.25 weight percent; and the stained fluid sample comprises a disaccharide dissolved in the aqueous liquid medium and the stained fluid sample comprises the disaccharide at a concentration in a range having a lower limit selected from the group consisting of 0.1 weight percent, 0.2 weight percent and 0.3 weight percent and an upper limit selected from the group consisting of 3 weight percent, 2 weight percent, 1 weight percent and 0.75 weight percent; and with one preferred range being from 0.1 weight percent to 2 weight percent and a more preferred range being from 0.2 weight percent to 1 weight percent.

49. The stained fluid sample of combination 48, wherein the liquid phase organic material comprises dimethyl sulfoxide (DMSO).

50. The stained fluid sample of combination 49, wherein the liquid phase organic material consists essentially of only DMSO.

51. The stained fluid sample of either one of combination 48 or combination 49, wherein the liquid phase organic material comprises acetonitrile.

52. The stained fluid sample of any one of combinations 48-51, wherein the disaccharide comprises one or more than one member selected from the group consisting of trehalose, sucrose, lactose, lactulose, melibiose, melibiulose, cellobiose, nigerose, isomaltose, isomaltulose, maltulose, rutinose, β-laminaribiose, and maltose.

53. The stained fluid sample of any one of combinations 48-52, wherein the disaccharide comprises trehalose.

54. The stained fluid sample of combination 53, wherein the disaccharide consists essentially of only trehalose.

55. The kit, product, method or stained fluid sample of any one of combinations 1-54, wherein the plurality of fluorogenic dyes in the liquid dye concentrate comprises a first fluorogenic dye for non-specific protein staining.

56. The kit, product, method or stained fluid sample of any one of combinations 1-55, wherein the plurality of fluorogenic dyes in the liquid dye concentrate comprises a second fluorogenic dye for non-specific nucleic acid staining.

57. The kit, product, method or stained fluid sample of any one of combinations 1-56, wherein the unassociated virus-size particles have a particle size of 2 microns or smaller, optionally 1 micron or smaller, further optionally 600 nanometers or smaller, further optionally 300 nanometers or smaller, further optionally 200 nanometers or smaller and further optionally 100 nanometers or smaller.

58. The kit, product, method or stained fluid sample of any one of combinations 1-57, wherein the unassociated virus-size particles have a particle size of at least 10 nanometers, optionally at least 20 nanometers, further optionally at least 30 nanometers, and further optionally at least 40 nanometers.

59. The kit, product, method or stained fluid sample of any one of combinations 1-58, wherein the unassociated virus-size particles are genetically modified.

60. The kit, product, method or stained fluid sample of any one of combinations 1-59, wherein the unassociated virus-size particles are viral vectors with genetically modified nucleic acid content.

61. The kit, product, method or stained fluid sample of any one of combinations 1-60, wherein the unassociated virus-size particles comprise viral particles, optionally virions or further optionally virus-like particles.

62. The kit, product, method or stained fluid sample of any one of combinations 1-59, wherein the unassociated virus-size particles comprise extracellular vesicles (optionally being small extracellular vesicles), optionally exosomes, or further optionally microvesicles.

63. The kit, product, method or stained fluid sample of any one of combinations 1-62, wherein an aromatic group susceptible to pi stacking in either one or both of a first fluorogenic dye and a second fluorogenic dye of the plurality of different fluorogenic dyes includes a heteroaromatic ring.

64. The kit, product, method or stained fluid sample of combination 63, wherein the heteroaromatic ring includes nitrogen as a heteroatom.

65. The kit, product, method or stained fluid sample of either one of combination 63 or combination 64, wherein the heteroaromatic ring includes oxygen as a heteroatom.

66. The kit, product, method or stained fluid sample of any one of combinations 1-65, wherein an aromatic group susceptible to pi stacking in either one or both of a first fluorogenic dye and a second fluorogenic dye of the plurality of different fluorogenic dyes includes a 6-member aromatic ring.

67. The kit, product, method or stained fluid sample of combination 66, wherein the 6-member aromatic ring is a homocyclic ring.

68. The kit, product, method or stained fluid sample of combination 67, wherein the 6-member aromatic ring is a heterocyclic ring.

69. The kit, product, method or stained fluid sample of any one of combinations 1-68, wherein an aromatic group susceptible to pi stacking in either one or both of a first fluorogenic dye and a second fluorogenic dye of the plurality of different fluorogenic dyes is part of a fused ring moiety.

70. The kit, product, method or stained fluid sample of combination 69, wherein the fused ring moiety comprises a 6-member homocyclic aromatic ring and a 5-member heterocyclic ring.

71. The kit, product, method or stained fluid sample of combination 70, wherein the 5-member heterocyclic ring is an aromatic ring.

72. The kit, product, method or stained fluid sample of any one of combinations 67, 70 and 71 wherein the heterocyclic ring comprises one or more heteroatom selected from the group consisting of nitrogen, oxygen, sulfur and combinations thereof.

73. The kit, product, method or stained fluid sample of any one of combinations 1-72, wherein at least one of a first fluorogenic dye or a second fluorogenic dye in the plurality of different fluorogenic dyes is a cyanine dye.

74. The kit, product, method or stained fluid sample of combination 73, wherein each of the first fluorogenic dye and the second fluorogenic dye is a cyanine dye.

75. The kit, product, method or stained fluid sample either one of combination 73 or combination 74, wherein the second fluorogenic dye is a merocyanine dye.

76. The kit, product, method or stained fluid sample of any one of combinations 73-75, wherein the first fluorogenic dye is a cyanine dye dimer.

77. The kit, product, method or stained fluid sample of combination 76, wherein the cyanine dimer is a dimer of an un-symmetrical cyanine dye.

The foregoing description of the present invention and various aspects thereof, indicating the examples presented above, has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

The description of a feature or features in a particular combination do not exclude the inclusion of an additional feature or features in a variation of the particular combination. Processing steps and sequencing are for illustration only, and such illustrations do not exclude inclusion of other steps or other sequencing of steps to an extent not necessarily incompatible. Additional steps may be included between any illustrated processing steps or before or after any illustrated processing step to an extent not necessarily incompatible.

The terms "comprising", "containing", "including" and "having", and grammatical variations of those terms, are intended to be inclusive and nonlimiting in that the use of such terms indicates the presence of a stated condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or any appropriate grammatical variation of such narrower terms). For example, a statement that something "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all. The term "at least a majority" means all or a majority part that is less than all. When reference is made to a "liquid medium" in which fluorogenic dyes are dissolved, such as in the case of the liquid medium of the liquid dye concentrate, it is meant the liquid medium of a liquid composition in which the fluorogenic dyes are dispersed in solution, and not including the fluorogenic dyes themselves. Such a liquid medium as used herein also does not include any suspended solids that may be carried by such a liquid composition. Such a liquid medium may include one or more than one normally-liquid components (e.g., DMSO and/or water and/or one or more other organic solvent components) and a liquid composition including the liquid medium may include one or more normally-solid materials (e.g., dissolved salts and other additives of buffer solutions) that may be in solution in the liquid medium of the liquid composition.

The description provided herein has been presented primarily with respect to flow cytometry evaluation of virus-size particles. However, the liquid dye concentrate, for example provided in the product of the first aspect or the kit of the second aspect may also be beneficially employed for staining fluid samples for fluorescent staining of other particles for evaluation, including staining larger particles (e.g., cells) for traditional flow cytometry and staining particles generally for fluorescent microscopy, where providing a stable stain composition with multiple fluorogenic dyes in a ready-to-use formulation in aqueous liquid medium would be beneficial, such as may be provided by the liquid dye concentrate of this disclosure. Accordingly, the invention of the product of the first aspect and the kit of the second aspect are not limited only to applications of flow cytometry of virus-size particles, and the method of flow cytometry evaluation of the third aspect and the stained fluid sample of the fourth aspect may be used for evaluation of virus-size particles by other evaluation methods that may employ the use of fluorogenic dyes (e.g., fluorescent microscopy) and with adaptation to include other particles instead that are not virus-size particles (e.g., cells) for evaluation of the other particles by flow cytometry or by such other evaluation methods that may employ the use of fluorogenic dyes.

What is claimed is:

1. A kit for preparing fluorescently stained fluid samples containing biological material for flow cytometry evaluation for particles in the biological material, the kit comprising:
   a liquid dye concentrate in a sealed first container, the liquid dye concentrate comprising a plurality of different fluorogenic dyes dissolved in a liquid medium, each different said fluorogenic dye having a different fluorescent emission signature for detection when bound to a said particle; and
   an aqueous sample dilution liquid for preparing aqueous diluted fluid samples containing biological material for flow cytometry evaluation for the particles, the aqueous sample dilution liquid being contained in a sealed second container;
   and wherein the liquid dye concentrate comprises:
      the liquid medium comprising liquid phase organic material at a concentration in a range of from 10 weight percent to 50 weight percent of the liquid medium, the organic material being a solvent for the plurality of fluorogenic dyes; or
      disaccharide dissolved in the liquid medium at a concentration in a range of from 1 weight percent to 45 weight percent of the liquid dye concentrate; or
      combinations thereof.

2. The kit of claim 1, wherein the sealed first container and the sealed second container are packaged together within a common packaging enclosure.

3. The kit of claim 1, wherein the aqueous sample dilution liquid comprises an aqueous buffer solution.

4. The kit of claim 1, comprising the liquid phase organic material in the liquid medium, and wherein the liquid medium is an aqueous liquid medium comprising a major proportion on a molar basis of water and a minor proportion on a molar basis of the liquid phase organic material in the liquid medium.

5. A kit for preparing fluorescently stained fluid samples containing biological material for flow cytometry evaluation for particles in the biological material, the kit comprising:
   a liquid dye concentrate in a sealed first container, the liquid dye concentrate comprising a plurality of different fluorogenic dyes in a liquid medium, each different said fluorogenic dye having a different fluorescent emission signature for detection when bound to a said particle; and
   an aqueous sample dilution liquid for preparing aqueous diluted fluid samples containing biological material for flow cytometry evaluation for the particles, the aqueous sample dilution liquid being contained in a sealed second container;
   wherein the liquid dye concentrate comprises the liquid medium comprising liquid phase organic material at a concentration in a range of from 10 weight percent to 50 weight percent of the liquid medium, or disaccharide dissolved in the liquid medium at a concentration in a range of from 1 weight percent to 45 weight percent of the liquid dye concentrate, or combinations thereof; and
   wherein the liquid phase organic material comprises dimethyl sulfoxide (DMSO).

6. The kit of claim 5, comprising the disaccharide dissolved in the liquid medium, and wherein the disaccharide comprises trehalose, sucrose, lactose, lactulose, melibiose, melibiulose, cellobiose, nigerose, isomaltose, isomaltulose, maltulose, rutinose, β-laminaribiose or maltose, or combinations thereof.

7. The kit of claim 5, wherein the disaccharide comprises trehalose.

8. A fluorescent stain product with multiple fluorogenic dyes for direct fluorescent staining of aqueous fluid samples containing biological materials with multiple fluorogenic dyes for flow cytometry evaluation of stained fluid samples for the particles, the fluorescent stain product comprising:
a liquid dye concentrate comprising a plurality of different fluorogenic dyes dissolved in a liquid medium, each different said fluorogenic dye having a different fluorescent emission signature for detection when bound to a said particle; and
a sealed container containing the liquid dye concentrate; and wherein the liquid dye concentrate comprises:
the liquid medium comprising liquid phase organic material at a concentration of from 10 weight percent to 50 weight percent of the liquid medium, the organic material being a solvent for the plurality of fluorogenic dyes; and
disaccharide dissolved in the liquid medium at a concentration in a range of from 1 weight percent to 45 weight percent of the liquid dye concentrate.

9. A method for flow cytometry evaluation of biological material for particles in the biological material, the method comprising:
providing an aqueous preliminary fluid sample with biological material in an aqueous liquid for flow cytometry evaluation for particles;
providing a liquid dye concentrate comprising a plurality of different fluorogenic dyes dissolved in a liquid medium, each different said fluorogenic dye having a different fluorescent emission signature for detection when bound to a said particle, and wherein the providing the liquid dye concentrate is in the absence of reconstituting the fluorogenic dyes from a dry form into the liquid medium;
preparing an aqueous stained fluid sample, comprising staining the preliminary fluid sample with liquid dye concentrate;
subjecting the stained fluid sample to flow cytometry in a flow cytometer to detect and count occurrences of the particles stained with at least one of the fluorogenic dyes;
and wherein the method further comprises the liquid medium comprising liquid phase organic material, the organic material being a solvent for the plurality of fluorogenic dyes, or the liquid dye concentrate comprising disaccharide dissolved in the liquid medium, or combinations thereof;
and wherein the stained fluid sample comprises a concentration of the liquid phase organic material in a range of from 0.25 weight percent to 2 weight percent and a concentration of the disaccharide in a range of from 0.1 weight percent to 3 weight percent.

10. The method of claim 9, wherein the staining the preliminary fluid sample comprises combining the preliminary fluid sample and the liquid dye concentrate at a volume ratio of volume of the liquid dye concentrate to volume of the preliminary fluid sample in a range of from 1:125 to 1:24.

11. The method of claim 9, wherein the providing the liquid dye concentrate comprises unsealing a first sealed container containing the liquid dye concentrate and removing from the unsealed container a quantity of the liquid dye concentrate for combining with the preliminary fluid sample during the staining, and wherein the first sealed container is in a kit, the kit comprising:
the liquid dye concentrate in a sealed first container, the liquid dye concentrate comprising a plurality of different fluorogenic dyes in a liquid medium, each different said fluorogenic dye having a different fluorescent emission signature for detection when bound to a said particle; and
an aqueous sample dilution liquid for preparing aqueous diluted fluid samples containing biological material for flow cytometry evaluation for the particles, the aqueous sample dilution liquid being contained in a sealed second container.

12. The method of claim 11, comprising:
providing a plurality of said preliminary fluid samples each with a portion of a biological material from a stock source and each diluted to different dilution ratios with the aqueous sample dilution liquid;
and separately subjecting each said stained fluid sample to the flow cytometry.

13. The method of claim 9, wherein the flow cytometry comprises:
hydrodynamically focusing a flow of the stained fluid sample with a sheath fluid; and
flowing the hydrodynamically focused stained fluid sample through a flow cell in which the flowing hydrodynamically focused stained fluid sample is subjected to excitation radiation to stimulate a fluorescent emission response from each of a first said fluorogenic dye and a second said fluorogenic dye on the particles stained with both the first fluorogenic dye and the second fluorogenic dye; and
detecting for both a first fluorescent emission signature of the first said fluorogenic stain staining a said particle and a second fluorescent emission signature of the second said fluorogenic stain staining a said particle;
wherein, the flowing comprises maintaining a flow rate of the hydrodynamically focused stained fluid sample through the flow cell in a range of from 300 nanoliters per minute to 6000 nanoliters per minute; and
separately detecting for each of the first fluorescent emission signature and the second fluorescent emission signature and time correlating detection of the first fluorescent emission signature and detection of the second fluorescent emission signature to determine a detection event indicative of an occurrence of a said particle stained with both the first fluorogenic dye and the second fluorogenic dye.

14. The method of claim 9, wherein the biological material comprises the particles, and the particles comprise unassociated virus-size particles having a particle size in a range of from 10 nanometers to 1 micron.

15. A stained fluid sample for flow cytometry evaluation for particles, the stained fluid sample comprising:
an aqueous liquid medium;
a biological material of interest for flow cytometry evaluation for the particles dispersed in the aqueous liquid medium; and
a plurality of different fluorogenic dyes dispersed in the aqueous liquid medium, each said fluorogenic dye having a different fluorescent emission signature and each containing at least one aromatic group susceptible to pi stacking, the plurality of different fluorogenic dyes including at least a first fluorogenic dye with a first fluorescent emission signature and a second fluorogenic dye with a second fluorescent emission signature that is different than the first fluorescent emission signature;

and wherein:
the aqueous liquid medium comprises liquid phase organic material at a concentration in a range of from 0.25 weight percent to 2 weight percent, the organic material being a solvent for the plurality of fluorogenic dyes; and
the stained fluid sample comprises disaccharide dissolved in the aqueous liquid medium and the stained fluid sample comprises the disaccharide at a concentration in a range of from 0.1 weight percent to 3 weight percent.

16. The method of claim 9, wherein:
the biological material comprises the particles and the particles comprise one of viral particles, virions, virus-like particles, extracellular vesicles, exosomes, particles having a size in a range of from 10 nanometers to 1 micron, or combinations thereof;
the liquid phase organic material comprises one of DMSO, acetonitrile, or combinations thereof;
the disaccharide comprises one of trehalose, sucrose, lactose, lactulose, melibiose, melibiulose, cellobiose, nigerose, isomaltose, isomaltulose, maltulose, rutinose, β-laminaribiose, maltose, or combinations thereof.

17. The method of claim 16, wherein the concentration of the liquid phase organic material is in a range of from 0.5 weight percent to 1.25 weight percent and the concentration of the disaccharide is in a range of from 0.2 weight percent to 1 weight percent.

18. The method of claim 9, wherein;
the liquid dye concentrate biological material comprises the particles and the particles comprise cells;
the liquid phase organic material comprises one of DMSO, acetonitrile, or combinations thereof; and
the disaccharide comprises one of trehalose, sucrose, lactose, lactulose, melibiose, melibiulose, cellobiose, nigerose, isomaltose, isomaltulose, maltulose, rutinose, 13-laminaribiose, maltose, or combinations thereof.

19. The method of claim 9, wherein the liquid dye concentrate comprises the liquid phase organic material and the disaccharide.

20. The kit of claim 4, wherein the liquid phase organic material comprises acetonitrile.

21. The kit of claim 4, wherein the concentration of the liquid phase organic material is in a range of from 15 weight percent to 35 weight percent.

22. The kit of claim 4, comprising the disaccharide dissolved in the liquid medium.

23. The kit of claim 1, comprising:
the disaccharide dissolved in the liquid medium at a concentration of from 6 weight percent to 24 weight percent of the liquid dye concentrate; and
the disaccharide comprising one of trehalose, sucrose, lactose, lactulose, melibiose, melibiulose, cellobiose, nigerose, isomaltose, isomaltulose, maltulose, rutinose, 13-laminaribiose or maltose, or combinations thereof.

24. The kit of claim 1, comprising an antibody stain for binding with an epitope of the particles.

25. The kit of claim 24, wherein the antibody stain is within the common packaging.

26. The kit of claim 5 comprising the disaccharide dissolved in the liquid medium.

27. The kit of claim 5, wherein the liquid medium comprises the DMSO at a concentration in a range of from 15 weight percent to 35 weight percent of the liquid medium.

28. The product of claim 8, wherein:
the concentration of the disaccharide is in a range of from 6 weight percent to 24 weight percent of the liquid dye concentrate;
the disaccharide comprises one of trehalose, sucrose, lactose, lactulose, melibiose, melibiulose, cellobiose, nigerose, isomaltose, isomaltulose, maltulose, rutinose, 13-laminaribiose or maltose, or combinations thereof;
the concentration of the liquid phase organic material is in a range of from 15 weight percent to 35 weight percent of the liquid medium; and
the liquid phase organic material comprises one of DMSO, acetonitrile, or combinations thereof.

29. The stained fluid sample of claim 15, wherein the liquid phase organic material comprises DMSO.

30. The stained fluid sample of claim 15, wherein the liquid phase organic material comprises acetonitrile.

31. The stained fluid sample of claim 15, wherein the disaccharide comprises one of trehalose, sucrose, lactose, lactulose, melibiose, melibiulose, cellobiose, nigerose, isomaltose, isomaltulose, maltulose, rutinose, 13-laminaribiose, maltose, or combinations thereof.

32. The stained fluid sample of claim 15, comprising a fluorescent antibody stain for binding with an epitope of the particles.

33. The stained fluid sample of claim 15, comprising the particles and wherein the particles comprise one of viral particles, virions, virus-like particles, extracellular vesicles, exosomes, particles having a size in a range of from 10 nanometers to 1 micron, or combinations thereof.

34. The stained fluid sample of claim 33, wherein:
the liquid phase organic material comprises one of acetonitrile, DMSO, or combinations thereof;
the concentration of the liquid phase organic material is in a range of from 0.5 weight percent to 1.25 weight percent;
the disaccharide comprises one of trehalose, sucrose, lactose, lactulose, melibiose, melibiulose, cellobiose, nigerose, isomaltose, isomaltulose, maltulose, rutinose, 13-laminaribiose, maltose, or combinations thereof; and
the concentration of the disaccharide is in a range of from 0.2 weight percent to 1 weight percent.

35. The stained fluid sample of claim 15, comprising the particles and wherein the particles comprise cells.

* * * * *